(12) United States Patent
Fogel et al.

(10) Patent No.: US 9,421,178 B2
(45) Date of Patent: *Aug. 23, 2016

(54) ACAMPROSATE FORMULATIONS, METHODS OF USING THE SAME, AND COMBINATIONS COMPRISING THE SAME

(71) Applicant: Synchroneuron Inc., Waltham, MA (US)

(72) Inventors: Barry S. Fogel, Lexington, MA (US); William D. Kerns, Harvard, MA (US); Kei-Lai Fong, Berkeley, CA (US)

(73) Assignee: Synchroneuron, Inc., Newton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/891,102

(22) Filed: May 9, 2013

(65) Prior Publication Data

US 2013/0310455 A1 Nov. 21, 2013

Related U.S. Application Data

(63) Continuation of application No. 13/853,876, filed on Mar. 29, 2013, which is a continuation of application No. 13/745,619, filed on Jan. 18, 2013, which is a continuation-in-part of application No. PCT/US2012/067507, filed on Dec. 2, 2012.

(60) Provisional application No. 61/649,137, filed on May 18, 2012, provisional application No. 61/566,550, filed on Dec. 2, 2011.

(51) Int. Cl.

| | |
|---|---|
| A61K 31/185 | (2006.01) |
| A61K 45/06 | (2006.01) |
| A61K 31/385 | (2006.01) |
| A61K 31/164 | (2006.01) |
| A61K 9/00 | (2006.01) |
| A61K 9/20 | (2006.01) |
| A61K 31/135 | (2006.01) |
| A61K 31/137 | (2006.01) |
| A61K 31/138 | (2006.01) |
| A61K 31/15 | (2006.01) |
| A61K 31/165 | (2006.01) |
| A61K 31/166 | (2006.01) |
| A61K 31/343 | (2006.01) |
| A61K 31/381 | (2006.01) |
| A61K 31/4515 | (2006.01) |
| A61K 31/4525 | (2006.01) |
| A61K 31/454 | (2006.01) |
| A61K 31/496 | (2006.01) |
| A61K 31/519 | (2006.01) |
| A61K 31/5377 | (2006.01) |
| A61K 31/5415 | (2006.01) |
| A61K 31/55 | (2006.01) |
| A61K 31/551 | (2006.01) |
| A61K 31/553 | (2006.01) |
| A61K 31/554 | (2006.01) |
| A61K 47/22 | (2006.01) |
| A61K 47/32 | (2006.01) |
| A61K 47/38 | (2006.01) |

(52) U.S. Cl.
CPC .......... *A61K 31/185* (2013.01); *A61K 9/0065* (2013.01); *A61K 9/2027* (2013.01); *A61K 9/2054* (2013.01); *A61K 31/135* (2013.01); *A61K 31/137* (2013.01); *A61K 31/138* (2013.01); *A61K 31/15* (2013.01); *A61K 31/164* (2013.01); *A61K 31/165* (2013.01); *A61K 31/166* (2013.01); *A61K 31/343* (2013.01); *A61K 31/381* (2013.01); *A61K 31/385* (2013.01); *A61K 31/454* (2013.01); *A61K 31/4515* (2013.01); *A61K 31/4525* (2013.01); *A61K 31/496* (2013.01); *A61K 31/519* (2013.01); *A61K 31/5377* (2013.01); *A61K 31/5415* (2013.01); *A61K 31/55* (2013.01); *A61K 31/551* (2013.01); *A61K 31/553* (2013.01); *A61K 31/554* (2013.01); *A61K 45/06* (2013.01); *A61K 47/22* (2013.01); *A61K 47/32* (2013.01); *A61K 47/38* (2013.01)

(58) Field of Classification Search
CPC .......................... A61K 31/185; A61K 9/2027
See application file for complete search history.

(56) References Cited

U.S. PATENT DOCUMENTS

| | | |
|---|---|---|
| 3,536,809 A | 10/1970 | Applezweig |
| 3,574,820 A | 4/1971 | Johnson et al. |

(Continued)

FOREIGN PATENT DOCUMENTS

| | | | |
|---|---|---|---|
| CA | 1040533 | 10/1978 | |
| CH | EP 1382331 B1 * | 10/2011 | ........... A61K 9/2086 |

(Continued)

OTHER PUBLICATIONS

PRNewsWire. StarCap1500® co-processed starch excipient receives pharmaceutical precedence of use in the European Union. Electronic Resource: [ http://www.prnewswire.com/news-releases/starcap-1500-co-processed-starch-excipient-receives-pharmaceutical-precedence-of-use-in-the-european-union-149484765.html]. Retrieved on Oct. 23, 2014.*

(Continued)

*Primary Examiner* — Timothy Thomas
(74) *Attorney, Agent, or Firm* — Choate, Hall & Stewart—LLP; Brenda Herschbach Jarrell

(57) ABSTRACT

Embodiments disclosed herein generally relate to acamprosate formulations, methods of use of the formulations, to methods of using the formulations in combination with at least one other medication, and to combination products and compositions comprising the formulations and at least one other medication, such as neuroleptic (antipsychotic) and/or antidepressant drugs.

9 Claims, 4 Drawing Sheets

(56) References Cited

U.S. PATENT DOCUMENTS

| | | |
|---|---|---|
| 3,598,123 A | 8/1971 | Zaffaroni |
| 3,845,770 A | 11/1974 | Theeuwes et al. |
| 3,901,232 A | 8/1975 | Michaels et al. |
| 3,916,899 A | 11/1975 | Theeuwes et al. |
| 3,944,064 A | 3/1976 | Bashaw et al. |
| 4,008,719 A | 2/1977 | Theeuwes et al. |
| 4,063,064 A | 12/1977 | Saunders et al. |
| 4,088,864 A | 5/1978 | Theeuwes et al. |
| 4,207,890 A | 6/1980 | Mamajek et al. |
| 4,339,428 A * | 7/1982 | Tencza .............. A61K 9/4808 424/451 |
| 4,404,183 A | 9/1983 | Kawata et al. |
| 4,434,153 A | 2/1984 | Urquhart et al. |
| 4,536,403 A | 8/1985 | Rooks |
| 4,690,820 A | 9/1987 | Simko |
| 4,690,822 A | 9/1987 | Uemura et al. |
| 4,702,918 A | 10/1987 | Ushimaru |
| 4,735,804 A | 4/1988 | Caldwell et al. |
| 4,758,436 A | 7/1988 | Caldwell et al. |
| 4,767,727 A | 8/1988 | Claussen et al. |
| 4,851,232 A | 7/1989 | Urquhart et al. |
| 4,861,598 A | 8/1989 | Oshlack |
| 4,871,548 A | 10/1989 | Edgren et al. |
| 4,970,075 A | 11/1990 | Oshlack |
| 4,992,278 A | 2/1991 | Khanna |
| 4,996,058 A | 2/1991 | Sinnreich |
| 5,002,772 A | 3/1991 | Curatolo et al. |
| 5,007,790 A | 4/1991 | Shell |
| 5,047,464 A | 9/1991 | Pogany et al. |
| 5,059,595 A | 10/1991 | Le Grazie |
| 5,073,543 A | 12/1991 | Marshall et al. |
| 5,120,548 A | 6/1992 | McClelland et al. |
| 5,217,712 A | 6/1993 | Pogany et al. |
| 5,273,758 A | 12/1993 | Royce |
| 5,354,556 A | 10/1994 | Sparks et al. |
| RE34,990 E | 7/1995 | Khanna et al. |
| 5,443,843 A | 8/1995 | Curatolo et al. |
| 5,458,887 A | 10/1995 | Chen et al. |
| 5,582,837 A | 12/1996 | Shell |
| 5,591,767 A | 1/1997 | Mohr et al. |
| 5,651,985 A | 7/1997 | Penners et al. |
| 5,674,533 A | 10/1997 | Santus et al. |
| 5,718,700 A | 2/1998 | Edgren et al. |
| 5,733,566 A | 3/1998 | Lewis |
| 5,736,159 A | 4/1998 | Chen et al. |
| 5,783,212 A | 7/1998 | Fassihi et al. |
| 5,840,754 A | 11/1998 | Guittard et al. |
| 5,912,268 A | 6/1999 | Guittard et al. |
| 5,972,389 A | 10/1999 | Shell et al. |
| 6,057,373 A | 5/2000 | Fogel |
| 6,120,803 A | 9/2000 | Wong et al. |
| 6,294,583 B1 | 9/2001 | Fogel |
| 6,340,475 B2 | 1/2002 | Shell et al. |
| 6,365,183 B1 | 4/2002 | Edgren et al. |
| 6,391,922 B1 | 5/2002 | Fogel |
| 6,403,120 B1 | 6/2002 | Sherman et al. |
| 6,426,087 B1 | 7/2002 | Saslawski et al. |
| 6,451,808 B1 | 9/2002 | Cowles |
| 6,488,962 B1 | 12/2002 | Berner et al. |
| 6,514,524 B1 | 2/2003 | Gryczke |
| 6,548,083 B1 | 4/2003 | Wong et al. |
| 6,635,280 B2 | 10/2003 | Shell et al. |
| 6,635,281 B2 | 10/2003 | Wong et al. |
| 6,682,759 B2 | 1/2004 | Lim et al. |
| 6,685,962 B2 | 2/2004 | Friedman et al. |
| 6,689,816 B2 | 2/2004 | Fogel |
| 6,723,340 B2 | 4/2004 | Gusler et al. |
| 6,797,283 B1 | 9/2004 | Edgren et al. |
| 7,405,238 B2 | 7/2008 | Markey et al. |
| 7,413,751 B2 | 8/2008 | Devane et al. |
| 7,438,927 B2 | 10/2008 | Berner et al. |
| 7,498,361 B2 | 3/2009 | Fogel |
| 7,514,100 B2 | 4/2009 | Oshlack et al. |
| 7,612,112 B2 | 11/2009 | Berner et al. |
| 7,731,989 B2 | 6/2010 | Berner et al. |
| 7,736,667 B2 | 6/2010 | Berner et al. |
| 7,976,870 B2 | 7/2011 | Berner et al. |
| 2004/0180088 A1 | 9/2004 | Dudhara et al. |
| 2005/0249798 A1 | 11/2005 | Mohammad |
| 2008/0167291 A1 | 7/2008 | Barlow et al. |
| 2008/0206350 A1 | 8/2008 | Gryczke |
| 2009/0304753 A1 | 12/2009 | Tsabari et al. |
| 2009/0304768 A1 | 12/2009 | Lapidot et al. |
| 2011/0091542 A1 | 4/2011 | Navon et al. |
| 2012/0077878 A1* | 3/2012 | Berner et al. .............. 514/578 |
| 2013/0143867 A1* | 6/2013 | Fogel et al. ............ 514/211.13 |
| 2013/0224292 A1* | 8/2013 | Fogel et al. ................ 424/457 |
| 2013/0245004 A1* | 9/2013 | Fogel et al. ............ 514/211.13 |
| 2013/0310456 A1 | 11/2013 | Fogel et al. |

FOREIGN PATENT DOCUMENTS

| | | |
|---|---|---|
| EP | 0661045 | 7/2002 |
| WO | WO 9427587 | 12/1994 |
| WO | WO 9519174 | 7/1995 |
| WO | WO 9529665 | 11/1995 |
| WO | WO 9530422 | 11/1995 |
| WO | WO 9600065 | 1/1996 |
| WO | WO 9608253 | 3/1996 |
| WO | WO 9613248 | 5/1996 |
| WO | WO 9625153 | 8/1996 |
| WO | WO 9626717 | 9/1996 |
| WO | WO 9626718 | 9/1996 |
| WO | WO 9632097 | 10/1996 |
| WO | WO 9637189 | 11/1996 |
| WO | WO 9637202 | 11/1996 |
| WO | WO 9718814 | 5/1997 |
| WO | WO 9733566 | 9/1997 |
| WO | WO 9737640 | 10/1997 |
| WO | WO 9747285 | 12/1997 |
| WO | WO 9748385 | 12/1997 |
| WO | WO 9811879 | 3/1998 |
| WO | WO 9815264 | 4/1998 |
| WO | WO 9833489 | 8/1998 |
| WO | WO 9855107 | 12/1998 |
| WO | WO 9906045 | 2/1999 |
| WO | WO 9912527 | 3/1999 |
| WO | WO 9917745 | 4/1999 |
| WO | WO 9921551 | 5/1999 |
| WO | WO 9929297 | 6/1999 |
| WO | WO 9929305 | 6/1999 |
| WO | WO 9930692 | 6/1999 |
| WO | WO-99/36064 A2 | 7/1999 |
| WO | WO 99/42086 * | 8/1999 |
| WO | WO 9942086 | 8/1999 |
| WO | WO-03/072087 A1 | 9/2003 |
| WO | WO-2008/101743 A2 | 8/2008 |
| WO | WO-2012/050922 A2 | 4/2012 |
| WO | WO 2013082573 | 6/2013 |
| WO | WO-2014/197744 A1 | 12/2014 |

OTHER PUBLICATIONS

Torrado et al. Chitosan-poly(acrylic) acid polyionic complex: in vivo study to demonstrate prolonged gastric retention. Biomaterials, vol. 25, Issue 5, Feb. 2004, pp. 917-923.*

Sungthongjeen et al. Design and evaluation of floating multi-layer coated tablets based on gas formation. European Journal of Pharmaceutics and Biopharmaceutics, 69, 2008, 255-263.*

Meshali et al.; "Preparation and Evaluation of Theophylline Sustained-Release Tablets"; 1996; Drug Development and Industrial Pharmacy; 22(4): 373-376.*

U.S. Appl. No. 14/297,388, filed Jun. 5, 2014. Fogel et al.

Burton S., et al. Intragastric distribution of ion-exchange resins: a drug delivery system for the topical treatment of the gastric mucosa. Phar. Pharm. 47(11), pp. 901-906 (1995).

Baldrick P. Pharmaceutical excipient development: the need for preclinical guidance. Regul. Toxicol. Pharmacal. 32(2):210-8 (2000).

Charman WN. Lipids, lipophilic drugs, and oral drug delivery—some emerging concepts. J Pharm Sci. 89(8):967-78 (2000).

(56) References Cited

OTHER PUBLICATIONS

Hammarberg et al. Acamprosate determinations in plasma and cerebrospinal fluid after multiple dosing measured by liquid chromatography—mass spectroscopy: A pharmacokinetic study in healthy volunteers. Ther Drug Monit, 32:489-496 (2010).
Garg S and Sharma S. Gastroretentive Drug Delivery System, Business Briefing, Pharmatech, pp. 160-166 (2003).
Nayak AK et al. Gastroretentive drug delivery systems, a review. Asian Journal of Pharmaceutical and Clinical Research, 3(1), pp. 1-10 (2010).
Saivin, et al. Clinical pharmacokinetics of acamprosate. Clin Pharmacokinet. 35(5):331-45 (1998).
Surana AS and Kotecha RK. An Overview on Various Approaches to Oral Controlled Drug Delivery System Via Gastroretention. Int'l J. Pharm. Sci. Rev. and Research; 2:68-72 (2010).
Anilkumar. Gastroretentive drug delivery system: an overview. Pharmainfo.net, vol. 6, Issue 1, Feb. (2008).
Wilde and Wagstaff. Acamprosate—A review of its pharmacology and clinical potential in the management of alcohol dependence after detoxification. Drugs 53:1039-53, (1997).
International search report and written opinion dated Jun. 3, 2014 for PCT/US2012/067507 filed Dec. 2, 2012.
Office Communications Issued in U.S. Appl. No. 13/745,619, filed on Jan. 18, 2013.
Office Communications Issued in U.S. Appl. No. 13/853,876, filed on Mar. 29, 2013.
Office Communications Issued in U.S. Appl. No. 13/891110, filed on May 9, 2013.
Office Communications Issued in U.S. Appl. No. 13/891,061, filed on May 9, 2013.
Dehghan, M.H.G. and Khan, F.N., Gastroretentive Drug Delivery Systems: A Patent Perspective, International Journal of Health Research, 2(1):23-44 (2009).
Thaakur, S. and Himabindhu, G., Effect of alpha lipoic acid on the tardive dyskinesia and oxidative stress induced by haloperidol in rats, Journal of Neural Transmission, 116:807-814 (2009).
European Search Report for EP 12853036.7, 5 pages (Mar. 25, 2015).
Singh, B. et al., Formulation and optimization of controlled release mucoadhesive tablets of atenolol using response surface methodology, AAPS PharmSciTech., 7(1) Article 3: E19-E28 (2006).
CAMPRAL6® (acamprosate calcium) Delayed-Release Tablets, Highlights of Prescribing Information, 11 pages (2004).
Excipients for Oral Solid Dosage Forms, Lubrizol Life Science Polymers, pp. 1-9 (2013).
Fleisher, D. et al., Drug, Meal and Formulation Interactions Influencing Drug Absorption After Oral Administration, Clin Pharmacokinet, 36(3):233-254 (1999).
Formulating Controlled Release Tablets and Capsules with Carbopol® Polymers, Lubrizol Pharmaceutical Bulletin, 31:pp. 1-22 (2011).
Grant, M. and Baldessarini, R., Possible improvement of neuroleptic-associated tardive dyskinesia during treatment with aripiprazole, The Annals of Pharmacotherapy, 39: p. 1953 (2005).
Guidance for Industry: Food-Effect Bioavailability and Fed Bioequivalence Studies, U.S. Department of Health and Human Services Food and Drug Administration Center for Drug Evaluation and Research (CDER), 12 pages (2002).
Lubrizol Corporation, Lubrizol Pharmaceutical Polymers for Controlled Release Tablets and Capsules, Pharmaceutical Bulletin 30:pp. 1-7 (2011).
Lubrizol Corporation, Molecular Weight of Carbopol® and Pemulen™Polymers, Technical Data Sheet 222:pp. 1-3 (2008).
STRIANT® (testosterone buccal system mucoadhesive) package insert, 16 pages (2003).
Sun, C. C. et al., Development of a High Drug Load Tablet Formulation Based on Assessment of Powder Manufacturability: Moving Towards Quality by Design, Journal of Pharmaceutical Sciences, 98:239-247 (2009).
TENUATE® (diethylpropion hydrochloride USP immediate-release & diethylpropion hydrochloride USP controlled-release) package insert, 8 pages (2003).
USP Pharmacists' Pharmacopeia, 3 Supplement, Second Edition, 166 pages (2009).

* cited by examiner

ACAMPROSATE FORMULATIONS, METHODS OF USING THE SAME, AND COMBINATIONS COMPRISING THE SAME

CROSS-REFERENCE TO RELATED APPLICATIONS

This application is a continuation of U.S. application Ser. No. 13/853,876, filed on Mar. 29, 2013, entitled "ACAMPROSATE FORMULATIONS, METHODS OF USING THE SAME, AND COMBINATIONS COMPRISING THE SAME," which is a continuation of U.S. application Ser. No. 13/745,619, filed on Jan. 18, 2013, entitled "ACAMPROSATE FORMULATIONS, METHODS OF USING THE SAME, AND COMBINATIONS COMPRISING THE SAME," which is a continuation in part of PCT Application No. PCT/US2012/067507, filed on Dec. 2, 2012, entitled "ACAMPROSATE FORMULATIONS, METHODS OF USING THE SAME, AND COMBINATIONS COMPRISING THE SAME," which claimed the benefit of priority under 35 U.S.C §119(e) of U.S. Provisional Application No. 61/566,550 filed on Dec. 2, 2011, and U.S. Provisional Application No. 61/649,137, filed on May 18, 2012, both entitled "METHODS OF USING ACAMPROSATE FORMULATIONS AND COMPOSITIONS COMBINING ACAMPROSATE FORMULATIONS WITH NEUROLEPTIC DRUGS," each of which is hereby incorporated herein by reference in its entirety and is to be considered a part of this specification.

BACKGROUND

1. Field

Embodiments disclosed herein generally relate to methods of use of improved formulations of acamprosate (calcium N-acetylhomotaurinate) and to compositions and use of compositions comprising medications, such as neuroleptic (antipsychotic) and/or antidepressant drugs, combined with improved formulations of acamprosate.

2. Description of the Related Art

Acamprosate (calcium N-acetylhomotaurinate) is the calcium salt of a derivative of the amino acid taurine. It is known to facilitate GABA-A neurotransmission and to modulate neuronal responses to the stimulation of both NMDA-type glutamate receptors and certain classes of metabotropic glutamate receptors. In particular, it reduces the response of the voltage-operated calcium channel to high levels of stimulation by glutamate. (Wilde & Wagstaff, Drugs 53:1039-53, 1997). Acamprosate is used clinically in the treatment of abstinent alcoholics to reduce or inhibit the craving for alcohol. Several U.S. patents (e.g., U.S. Pat. Nos. 6,057,373, 6,294,583, 6,391,922, 6,689,816, and 7,498,361; each of which is incorporated herein by reference in its entirety) describe the use of acamprosate to treat neuropsychiatric disorders, including tardive dyskinesia and other movement disorders induced by chronic exposure of patients to neuroleptic (antipsychotic) drugs, Tourette's syndrome, and mental disorders such as posttraumatic stress disorder (PTSD) and obsessive-compulsive disorder (OCD).

SUMMARY

Acamprosate is a compound with high solubility and low permeability—Class III under the Biopharmaceuticals Classification System (BCS). The bioavailability of BCS Class III compounds tends to be low because the absorption of such compounds occurs either via diffusion—which is slow and inefficient because of the low permeability—or via specialized transporters in the membranes of intestinal mucosal cells—which may not exist, may poorly bind the compound, or may be easily saturated, implying zero-order kinetics.

Some embodiments herein are related to methods and compositions where the pharmacokinetics (PK) of acamprosate are altered. The PK of acamprosate can be altered, for example, when the acamprosate is formulated for controlled release by gastroretentive (GR) delivery systems—solid state dosage forms that are retained in the stomach for several hours, during which time the formulations gradually release the acamprosate into the gastric milieu.

There are several different methods for creating GR delivery systems; they have been described in review articles (not an exhaustive or limiting list) over the past several years, e.g., Pharmainfo.net, Volume 6, Issue 1, Feb. 3, 2008; Garg S and Sharma S, Gastroretentive Drug Delivery System, Business Briefing, Pharmatech 2003, Nayak A K, Maji R, Das B, Gastroretentive Drug Delivery Systems, a Review, Asian Journal of Pharmaceutical and Clinical Research, Volume 3, Number 1, January-March 2010, pp 1-10; each of which is incorporated herein by reference in its entirety. These systems all can be applied to acamprosate. Their effect is to deliver the drug to the proximal duodenum at a controlled rate, usually over several hours.

Some embodiments described herein are based upon the discovery of benefits associated with formulating acamprosate utilizing technology, such as GR formulation technology. Without being limited thereto, two practical benefits of the altered PK discovered when using such formulations are efficacy with less frequent dosing and avoidance of dose-dependent side effects related to the $C_{max}$, which is lower with GR formulations than with immediate-release (IR) formulations containing the same amount of acamprosate. An additional non-limiting benefit is the potential efficacy of a lower total oral dose of the drug for its clinical indication. Furthermore, even in embodiments where the GR system does not offer greater bioavailability—i.e., a larger area under the time-concentration curve (AUC) for a given oral dose—it can increase the efficacy of an oral dose by increasing the target site residence time at which the concentration exceeds a minimal threshold for efficacy.

Embodiments described herein generally relate to the use of improved formulations of acamprosate and other salts of N-acetylhomotaurine or other related compounds. Some particular embodiments relate to formulations based on gastric-retentive (GR) delivery systems. Some embodiments relate to the use of improved formulations of acamprosate to treat neuropsychiatric disorders including tardive dyskinesia using dosages and dosage schedules not heretofore known to be efficacious. These dosages and dosage schedules can provide greater convenience and greater tolerability of treatment, and thus greater effectiveness of treatment because of better treatment adherence and tolerability of dosages sufficient for more complete relief of symptoms.

In some aspects, the improved formulations can be used to treat conditions, such as those listed above and elsewhere herein, with total daily dosages of acamprosate of less than 1 gram, given on a once-daily or twice-daily schedule, for example. This contrasts with heretofore-described therapeutic use of the currently-marketed enteric-coated acamprosate tablets. These must be given in doses of 2 grams or more per day to be efficacious in treating alcoholism, usually on a three times daily schedule and many patients require 2 grams or more to get relief of symptoms.

The efficacy of the lower doses is not necessarily based on the improved formulations being bioequivalent to higher doses of the currently-marketed enteric coated preparation. In fact the total AUC produced by the lower doses of the new formulations may be, in some embodiments, equal to or significantly lower than those produced with usual doses of the currently-marketed formulations, and in some embodiments the $C_{max}$ produced by the new formulations can be lower than that produced with the currently marketed formulation at a dose with equal efficacy.

Some embodiments also concern compositions and use of fixed-dose combinations of improved formulations of acamprosate with first-generation neuroleptic (antipsychotic) drugs, second generation neuroleptic drugs, selective serotonin reuptake inhibitors (SSRIs), serotonin norepinephrine reuptake inhibitors (SNRIs), or the anti-nausea drug metoclopramide. For example, the decreased dosage amount and frequency of dosing made possible by the improved formulations makes it feasible to formulate fixed-dose combinations of acamprosate and other medications, such as first-generation neuroleptic drugs. The fixed dose combinations with neuroleptics, for example, can provide effective treatment of psychosis with a lesser risk of metabolic side effects than seen with second-generation neuroleptic drugs, a lesser risk of tardive dyskinesia than seen with first and second generation neuroleptic drugs given alone, and with, unexpectedly, increased relief of mental symptoms compared with first-generation neuroleptic drugs given alone.

Some embodiments relate to combinations of from 100 mg to less than 1 gram (e.g., 800 mg) of acamprosate with a drug from a second class, for example, where the second drug is given in a dose ranging from half of the lower end of its usual dosage range to the upper end of its dosage range. The combination pill may be given either once or twice a day to treat a neuropsychiatric disorder, for example.

As noted, some embodiments relate to combinations of acamprosate combined with a second medication, such as for example, a neuroleptic medication. The fixed dose compositions comprising a first or second generation neuroleptic combined with an improved formulation of acamprosate can be used to treat any of the disorders treated with, for example, neuroleptic drugs or metoclopramide, including schizophrenia, schizoaffective disorder, bipolar disorder, major depression, delusional disorder, organic psychoses, delirious agitation, or nausea and vomiting. They can be given for this purpose on a once-daily or twice-daily schedule (or more if desired), typically with a single pill given each time. They can provide for a given dosage of neuroleptic, equal or greater benefit for the neuropsychiatric disorder or symptoms being treated, and can offer greater relief of anxiety and agitation when these are among the symptoms. Compared with the same dose of a first-generation neuroleptic given without acamprosate, these combinations entail a lower risk of tardive dyskinesia and other tardive movement disorders, and they cause movement disorder of lesser severity, if they cause one at all. In contrast with second-generation neuroleptics of equal therapeutic efficacy, these combinations can carry a lesser risk of significant metabolic disturbances including weight gain, glucose intolerance, and increased risk of atherosclerotic cardiovascular disease.

In the case of acamprosate combined with a neuroleptic, the combination can reduce the risk of tardive dyskinesia (TD) associated with giving the neuroleptic drug. Also, unexpectedly, the combination has additional benefits for the patient's mental status, such as decreased anxiety and/or agitation (as shown in the patient example). If the patient has pre-existing TD associated with cognitive impairment the acamprosate may also have, as claimed in prior patents, improvement in cognition. The action of acamprosate to treat—and consequentially to prevent the manifestation of—tardive dyskinesia, combined with the additional benefit of improving some mental symptoms—makes higher-potency and first-generation neuroleptic drugs more attractive when they are given in combination with acamprosate. At present the first-generation, high-potency neuroleptic drugs are avoided because they are more likely than second-generation neuroleptic drugs to produce tardive dyskinesia. However, those drugs are no less efficacious in treating psychosis than the second-generation drugs (with the sole exception of clozapine), which usually are more expensive, and which have serious metabolic effects with potentially life-threatening consequences. It is rational to combine even second-generation neuroleptics with acamprosate, because those drugs still carry some risk of TD, and the additional psychiatric benefit can still apply. Tables 10 and 11 below show non-limiting examples of the dose ranges for the neuroleptic drugs and the GR acamprosate formulation to be used in fixed dose combinations.

Some embodiments relate to compositions or methods of using compositions where the compositions further include a substance to induce a fed state in a patient. For example, the compositions can include alpha-lipoic acid, either as racemic alpha-lipoic acid or as R enantiomer of alpha-lipoic acid. In some aspects of the above uses, compositions or methods, the alpha-lipoic acid can be in a dosage of from about 40 to 600 mg or any value or sub range there between. In some aspects, the alpha-lipoic acid can be in a dosage of from about 100 to about 300 mg, or any value or sub range there between. In some aspects, the alpha-lipoic acid can be at least part of a gastric-retentive composition. In some aspects, the alpha-lipoic acid can at least partially be in the coating of the gastric-retentive system. In some aspects, the alpha-lipoic acid can be incorporated into a gastric-retentive system. In some aspects, the gastric-retentive system may be designed to release the alpha-lipoic acid within a period of time after ingestion, for example, the first hour after ingestion. In some aspects, alpha-lipoic acid may be included in a formulation or dosage form that also includes acamprosate, where the acamprosate is in a dose, for example, of 100 to less than 1 gram (e.g., 800-900 mg), or any value or sub range there between. In some aspects, alpha-lipoic acid may be included in a formulation or dosage form that includes acamprosate and that further includes a second medication, for example, a neuroleptic (antipsychotic) drug.

Also presented herein is a composition comprising acamprosate in a dose of about 100 to less than 1 gram (e.g., 100-700 mg or 100-900 mg; or any value or sub range there between) and alpha-lipoic acid in a dosage of about 100 to about 600 mg (or any value or sub range there between).

Also presented herein is a composition comprising alpha-lipoic acid in a dosage of about 100 to about 300 mg in a gastric-retentive composition comprising acamprosate and another medication (e.g., a neuroleptic (antipsychotic) drug), for example, as active pharmaceutical ingredients.

Some embodiments relate to methods of treating a neuropsychiatric disorder, which methods can include for example, administering to a patient in need thereof a total daily dosage of acamprosate of less than 1000 mg, wherein the acamprosate is administered once or twice daily to achieve the total daily dosage, and the administered acamprosate is in a composition that is formulated to release at least 50% of the acamprosate within the stomach of the recipient at a controlled rate over a 4-8 hour period.

In some aspects the composition can be formulated to release from about 50% to 99% of the acamprosate in the stomach. The composition may include for example, one or more gastric retentive excipients, one or more controlled release excipients, or one or more gastric retentive excipients and one or more controlled release excipients. The one or more gastric retentive excipients can be, for example, a floating excipient that is non-effervescent, a floating excipient that is effervescent, a bioadhesive excipient, a mucoadhesive excipient, an excipient that swells, an excipient that expands, a magnetic excipient, and the like. The one or more controlled release excipients can include, for example, a technology that forms a matrix, forms a coated bead, is osmotic or acts by ion exchange. The administered composition may be formulated to achieve a mean AUC for acamprosate that is greater than the mean AUC for an immediate release composition of a acamprosate, to have a $C_{max}$ for acamprosate that is less than the $C_{max}$ for an immediate release composition, and/or to have a $T_{max}$ for acamprosate that is delayed compared to the $T_{max}$ for an immediate release composition.

The composition may include, for example, one or more polymers that promote retention in the stomach of the recipient, for example, one or more of CARBOPOL® 974P (carbomer homopolymer type B) and carboxymethylcellulose. The polymers may be present in any suitable amount or range, for example, in some non-limiting embodiments from about 3% to 70% or any range or value within that broader range. For example, one or more hydrophilic polymers can be present in an amount of about 5% to about 20%.

The acamprosate can be administered once daily or twice daily for example. The administered once or twice daily acamprosate respectively can be a dosage of less than 1 gram, for example, in a dosage of 200 mg to 450 mg or 350 mg to 900 mg. Without being limited thereto, when administered the acamprosate can be administered as one or two units of a dosage form, for example, one or two pills, tablets or capsules. The single unit of a dosage form or the multiple units of a dosage form can have, for example, a total weight of less than 1200 mg. For example, in some embodiments herein, the total unit dosage form wait can be between 400 and 1200 mg, between 500 and 1200 mg, between 600 and 1200 mg, or any value or sub range within those ranges.

The methods further can include administering the acamprosate to a patient in a fed state or can include inducing a fed state in the patient. The neuropsychiatric disorder can be for example, tardive dyskinesia and other movement disorders induced by chronic exposure of patients to neuroleptic (antipsychotic) drugs, Tourette syndrome, posttraumatic stress disorder (PTSD) obsessive-compulsive disorder (OCD), and the like.

Some embodiments relate to improved methods of treating tardive dyskinesia with acamprosate, the improvement comprising providing an acamprosate dosage form once or twice per day wherein the dosage form comprises less than 1 gram of acamprosate, for example, from 50 to 900 mg of acamprosate (more preferably 50-500 mg), which dosage form upon administration releases acamprosate into the stomach of a patient at a controlled rate over a period from 3 to 10 hours, wherein the total daily dose of acamprosate provided is less than 1000 mg. In some aspects at least 50% of the acamprosate is released into the stomach within at least 3-4 hours.

Some embodiments relate to compositions that include acamprosate in a dosage of less than 1 gram or less than 900 mg that is formulated to retain the composition in the stomach of the recipient and to control the release of the acamprosate for a period of time sufficient to release at least 50% of the acamprosate from the composition into the stomach within a 4 hour period and to release acamprosate at a controlled rate over a period of 4 to 8 hours, wherein at least 90% of the acamprosate is released from the composition within 8 hours.

The composition can include for example, a gastric retentive technology, a controlled release technology, or both a gastric retentive and a controlled release technology. The one or more gastric retentive excipients are selected from the group consisting of a floating excipient that is non-effervescent, a floating excipient that is effervescent, a bioadhesive excipient, a mucoadhesive excipient, an excipient that swells, an excipient that expands, a magnetic excipient, and the like. The one or more controlled release excipients can include, for example, a technology that forms a matrix, that forms a coated bead, that is osmotic, that acts by ion exchange, or the like. The composition may include, for example, one or more polymers, such as one or more of CARBOPOL® 974P (carbomer homopolymer type B) and carboxymethylcellulose, and the like. The composition can be formulated such that upon administration to a recipient the mean AUC for acamprosate is equal to or greater than the mean AUC For an immediate release composition of a acamprosate, the $C_{max}$ for acamprosate is less than the $C_{max}$ for an immediate release composition, and/or the $T_{max}$ for acamprosate is longer than for immediate release acamprosate.

The acamprosate dosage can be, for example, between less than 1 gram (e.g., 100 mg and 800 mg) or any value or range within that range. The composition can be formulated, for example, as a tablet, a pill, a capsule, or the like. The composition further may include, for example, alpha lipoic acid, where the alpha lipoic acid is either racemic alpha lipoic acid or the R-enantiomer of alpha-lipoic acid, and the dosage of alpha lipoic acid is between 50 mg and 600 mg.

Some embodiments relate to methods of treating a neuropsychiatric disorder by administering to a patient in need thereof a composition as set forth above or elsewhere herein, wherein the total daily dosage of acamprosate administered is less than 1000 mg, wherein the composition is administered once or twice daily to achieve the total daily dosage.

Some embodiments relate to combination products that include, for example, a composition as described above and elsewhere herein and at least a second medication that includes one or more of an antipsychotic (neuroleptic) medication, a selective serotonin reuptake inhibitor (SSRI), a serotonin-norepinephrine reuptake inhibitor (SNRI), an antidepressant, an anti-anxiety medication, or the like. The antipsychotic medication can be, for example, a first or a second generation antipsychotic. The first or a second generation antipsychotic can be for example, one or more of thioridazine, chlorpromazine, thiothixene, trifluoperazine, fluphenazine, haloperidol, perphenazine, loxapine, molindone, metoclopramide, aripiprazole, asenapine, iloperidone, lurasidone, olanzapine, paliperidone, quetiapine, risperidone, ziprasidone, and the like. The SSRI or SNRI can be, for example, one or more of citalopram, desvenlafaxine, duloxetine, escitalopram, fluoxetine, fluvoxamine, milnacipran, paroxetine, sertraline, venlafaxine, and the like. The product may include, for example, a single dosage form unit that includes, consists or consists essentially of both acamprosate and at least one second medication.

Some embodiments relate to methods of treating a neuropsychiatric disorder, for example, by administering to a patient in need thereof a combination product as described above, and elsewhere herein, wherein the total daily dosage of acamprosate administered is less than 1000 mg, wherein the composition is administered once or twice daily to achieve the total daily dosage. The product can be or may include, for example, a pill, a tablet, a capsule or the like comprising acamprosate and at least one second medication. Still some embodiments relate to methods of reducing the risk or delaying the onset of tardive dyskinesia comprising administering to a patient in need thereof a combination product as described herein, wherein the total daily dosage of acamprosate administered is less than 1000 mg, wherein the composition is administered once or twice daily to achieve the total daily dosage. The product can be or may include, for example, a pill, a tablet, a capsule or the like comprising acamprosate and at least one second medication.

Also, some embodiments relate to methods of or uses of acamprosate for improving compliance with an acamprosate treatment regimen. The methods can include for example, providing to a patient a total daily dosage of acamprosate of less than 1 gram (e.g., 900 mg) and administering an effective amount of an acamprosate formulation once or twice daily, which formulation is formulated to release at least 50% of the acamprosate within the stomach of the recipient at a controlled rate over a 4-8 hour period. In some aspects, at least 50% is released within the first 4 hours. In some aspects, at least 90% is released from the composition within 8 hours. In some aspects, the patient can be a patient is selected, identified or by virtue of having been at least partially non-compliant with a previous treatment regimen. The treatment regimen can include, for example, alcoholism, treatment of a movement disorder, treatment of anxiety, treatment of depression, and the like.

Some embodiments relate to methods of or uses of acamprosate for reducing anxiety in a patient receiving a neuroleptic, anxiety or antidepressant medication. The methods can include for example, providing to a patient a total daily dosage of acamprosate of less than 1 gram (e.g., 900 mg) and administering an effective amount of an acamprosate formulation once or twice daily, which formulation is formulated to release at least 50% of the acamprosate within the stomach of the recipient at a controlled rate over a 4-8 hour period. In some aspects, at least 50% is released within the first 4 hours. In some aspects, at least 90% is released from the composition within 8 hours. The methods further can include, for example, identifying a patient suffering from anxiety despite receiving one of said medications or a patient in need of at least some reduction in anxiety despite receiving one of said medications.

Some embodiments relate to methods for or uses of acamprosate for reducing acamprosate side effects associated with treatment with dosages of greater than 1 gram. The methods can include, for example, administering to a patient in need thereof a total daily dosage of acamprosate of less than 1000 mg, wherein the acamprosate is administered once or twice daily to achieve the total daily dosage, and the administered acamprosate is in a composition that is formulated to release at least 50% of the acamprosate within the stomach of the recipient at a controlled rate over a 4-8 hour period. In some aspects, at least 50% is released within the first 4 hours. In some aspects, at least 90% is released from the composition within 8 hours. The side effect can be, for example, nausea and/or vomiting.

Some embodiments relate to methods of or uses of acamprosate for treating alcohol dependence comprising administering to a patient in need thereof a total daily dosage of acamprosate of less than 1000 mg, wherein the acamprosate is administered once or twice daily to achieve the total daily dosage, and the administered acamprosate is in a composition that is formulated to release at least 50% of the acamprosate within the stomach of the recipient at a controlled rate over a 4-8 hour period. In some aspects, at least 50% is released within the first 4 hours. In some aspects, at least 90% is released from the composition within 8 hours.

A method of treating alcohol dependence, comprising administering an effective amount of a pharmaceutical formulation comprising acamprosate to a patient in need thereof, wherein the formulation is formulated with one or more gastroretentive technologies and one or more controlled release technologies, which one or more gastroretentive technologies is selected from the group consisting of floating—non-effervescent, floating—effervescent, bioadhesive, mucoadhesive, swelling, expanding, and magnetic and which one or more controlled release technologies is selected from the group consisting of matrix, coated beads, osmotic, and ion exchange. In some aspects, the methods of treating alcoholism can include GR acamprosate plus alpha lipoic acid; the combination pill being taken either in the fed state or in the fasting state.

Furthermore, some embodiments relate to methods of or uses of acamprosate for treating a neuropsychiatric disorder, comprising administering once or twice daily a composition comprising acamprosate in a composition that releases at least 50% of the acamprosate at a controlled rate over a 4-8 hour period, and wherein the total daily dosage of acamprosate is less than 1000 mg. In some aspects, at least 50% is released within the first 4 hours. In some aspects, at least 90% is released from the composition within 8 hours.

Some embodiments relate to uses of acamprosate in the treatment of a neuropsychiatric disorder, wherein the acamprosate is administered once or twice daily as part of a composition comprising the acamprosate, wherein the composition releases at least 50% of the acamprosate at a controlled rate over a 4-8 hour period, and wherein the total daily dosage of acamprosate is less than 1000 mg. In some aspects, at least 50% is released within the first 4 hours. In some aspects, at least 90% is released from the composition within 8 hours. The disorder can be, for example, schizophrenia, schizoaffective disorder, bipolar disorder, major depressive disorder, delusional disorder, organic psychoses, Tourette Syndrome, and the like. Some embodiments relate to uses of acamprosate in the treatment of a neuropsychiatric disorder, wherein the acamprosate is formulated for once or twice daily administration in a composition that releases the acamprosate at a controlled rate over a 4-8 hour period, and wherein the total daily dosage of acamprosate is less than 1000 mg. In some aspects, at least 50% is released within the first 4 hours. In some aspects, at least 90% is released from the composition within 8 hours.

Some embodiments relate to compositions that include for example, a fixed dose of acamprosate in a gastroretentive controlled-release formulation where the dose of acamprosate is less than 1 gram (e.g., between 50 and 900 mg). Also, some embodiments relate to compositions that include a fixed dose of acamprosate in a gastroretentive controlled-release formulation and a fixed dose of a first-generation neuroleptic or a second-generation neuroleptic, a second generation neuroleptic or a fixed dose of metoclopramide, where the dose of acamprosate is less than 1 gram (e.g., between 50 and 900 mg). The dosage of the first-generation neuroleptic can be, for example, ½ of its lowest approved dosage up to its highest approved dosage, for example, 50% of its lowest approved dosage up to 90% of its lowest approved dosage.

Some embodiments relate to improved method of treating a mental disorder with a first or second generation neuroleptic, the improvement comprising administering a composition that comprises acamprosate in an amount of less than 1 gram, for example, 50 to 900 mg (or any value or sub range of less than 1 gram), and a first-generation neuroleptic, wherein the composition is formulated to release at least 50% of the acamprosate into the stomach of the recipient over a 4 to 8 hour period. The mental disorder can be, for example, one or more of schizophrenia, schizoaffective disorder, bipolar disorder, major depressive disorder, delusional disorder, organic psychosis, or Tourette Syndrome.

It should be understood that in the methods, uses and compositions described herein, that acamprosate can be substitute for by or included with any other salt or analog, for example, one more of sodium N-acetylhomotaurinate, magnesium N-acetylhomotaurinate, or lithium N-acetylhomotaurinate at the same milligram dose and/or free acid equivalent dose at the same milligram dose.

Still further embodiments relate to the inclusion of a substance to induce a fed mode in the patient, for example, in order minimize or reduce stomach clearance so as to maintain acamprosate in the stomach for a longer period of time. The methods, uses, products, formulations and compositions described herein, further may include, for example, alpha lipoic acid in an amount of 50 mg to 700 mg or any amount or sub range therein (e.g., 100-500 mg.). The alpha lipoic acid can be, for example, either racemic alpha lipoic acid, an enriched racemic mixture for one enantiomer or an enantiomer of alpha lipoic acid, such as the R enantiomer. The alpha lipoic acid can be included, for example, at least partially in the coating of a formulation. The formulation further can include a gastric-retentive system. In some aspects the alpha lipoic acid can be incorporated into a gastric retentive system. For example, a gastric retentive systems designed to release the alpha lipoic acid within the 30-120 minutes hours after ingestion. The alpha lipoic acid can be combined with acamprosate in a dosage of 100 to 700 mg (or any value or sub range there between such as 500 mg). Such compositions can include the alpha lipoic acid in combination with acamprosate and in combination with a neuroleptic (antipsychotic) drug. In some aspects the alpha-lipoic acid can be in a dosage of 100 to 300 mg in a gastric-retentive composition comprising a neuroleptic (antipsychotic) drug and acamprosate as active pharmaceutical ingredients.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIG. 1 illustrates the results for dog 1 from the study.

DETAILED DESCRIPTION

Introduction

Figure 1:
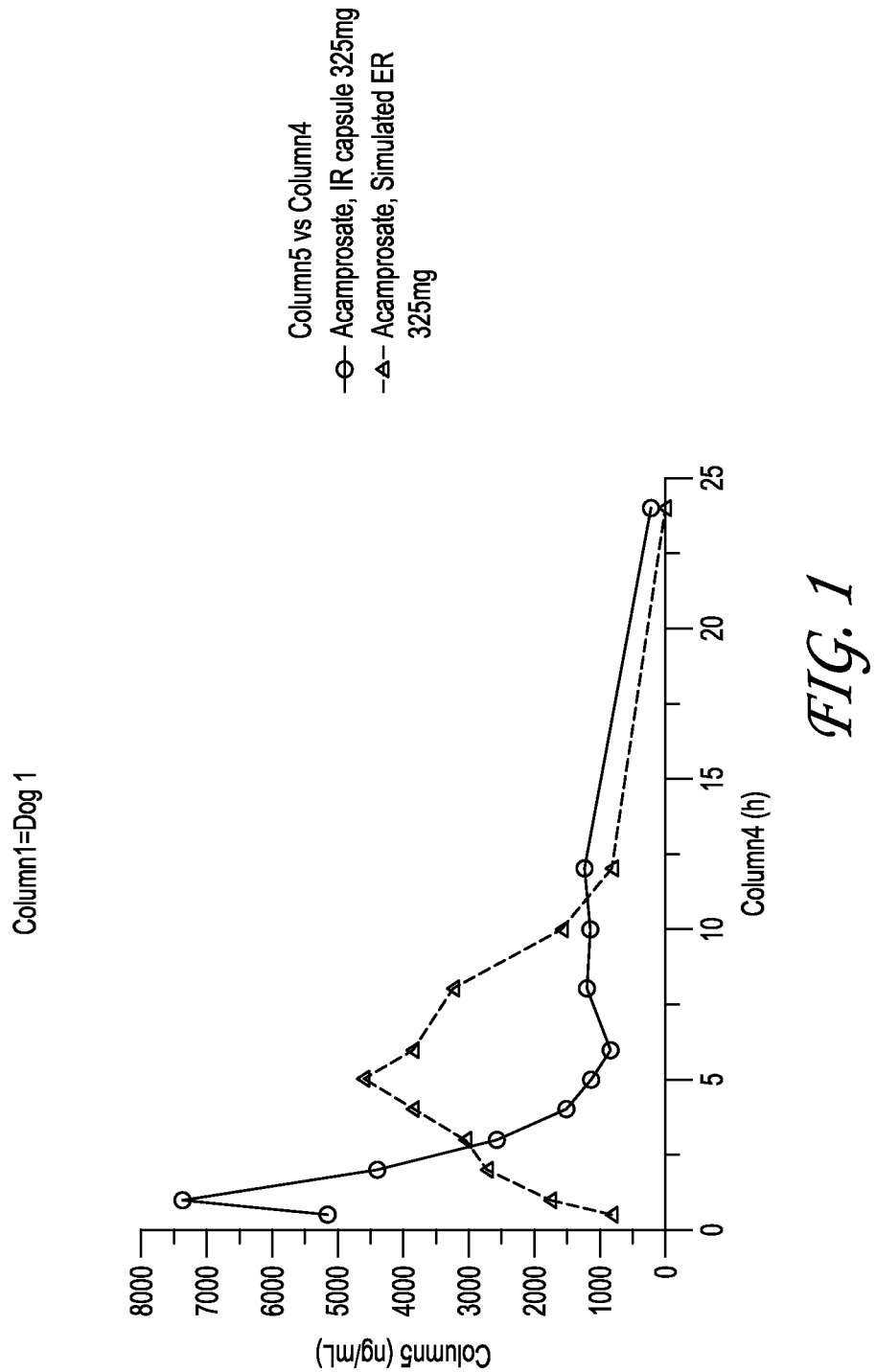
FIG. 1 illustrates the pharmacokinetic plot of immediate release versus simulated GR controlled-release acamprosate from a pharmacokinetic study (see EXAMPLE 3 below) conducted in four dogs (beagles).

Acamprosate (calcium bis acetyl-homotaurine; [3-(acetylamino)-1-propanesulfonic acid] calcium salt), is a derivative of the amino acid taurine) with effects on both GABA and glutamate-mediated neurotransmission. It is approved in several countries for the treatment of alcoholism—specifically, the inhibition of craving for alcohol in alcohol-dependent patients who are currently abstinent. For this purpose acamprosate has limited effectiveness; some controlled studies have failed to show efficacy, and adoption of the drug in practice has not been widespread. Clinical experience, described in the specification of several issued US patents, has shown acamprosate to be impressively efficacious in the treatment of tardive dyskinesia and other movement disorders, and in recurrent unwanted stereotypic movements, behaviors, perceptions, or thoughts, such as those that occur in obsessive-compulsive disorder, tic disorders, Tourette Syndrome, post-traumatic stress disorder, depression, and schizophrenia. The therapeutically active moiety in acamprosate is the acetylhomotaurine ion; thus, in any of the therapeutic applications of acamprosate described here and elsewhere the drug can be replaced by another salt of the same anion, with either a univalent or divalent cation—e.g., sodium acetylhomotaurinate, lithium acetylhomotaurinate, or magnesium acetylhomotaurinate. For purposes of the embodiments described herein, acamprosate (or another salt of acetylhomotaurine) can be used alone or in combination to treat various conditions characterized by recurrent, unwanted, stereotypic movements, behaviors, perceptions, or thoughts, including without limitation movement disorders (e.g., hyperkinetic movement disorders such as tardive dyskinesia ("TD"), tardive dystonia, tardive akathisia, peak-dose dyskinesia associated with Parkinson's disease treated with levodopa, dystonia, tics, Tourette Syndrome, chorea associated with Huntington's disease) obsessive-compulsive disorder, posttraumatic stress disorder (PTSD), recurrent intrusive thoughts in depression and stereotypic behavior in schizophrenia and autism.

TD is a chronic disorder of the nervous system, characterized by involuntary, irregularly rhythmic movements most often involving the mouth, tongue, and facial muscles. Choreatic or dystonic movements of the extremities can be involved, as can dystonic movements of the neck or trunk, and rocking movements of the trunk. TD with prominent limb movements most often is tardive dystonia, a subtype of TD tends to be severe, disabling, and difficult to treat. TD can be accompanied by tardive akathisia, an irresistible impulse to move which is often manifest as continual restless movements of the legs. Another potential accompaniment is disruption of respiratory movements leading to irregular breathing and subjective shortness of breath—respiratory dyskinesia. Most cases of TD are caused by long-term use of neuroleptics (antipsychotic drugs); the remainder are caused by chronic use of dopamine blocking drugs such as metoclopramide or prochlorperazine that are given to relieve or to prevent nausea and vomiting. However, there are numerous well-documented cases in which those drugs have induced TD after only a few weeks of exposure. Unlike many drug side effects tardive dyskinesia can actually get worse when the causative drug is discontinued, and the condition can persist for months, years, or even permanently afterwards. The prevalence of tardive dyskinesia with long-term treatment with first-generation antipsychotic drugs is over 25%, and even higher in elderly patients.

Second-generation antipsychotic drugs are associated with a lower but still significant prevalence of tardive dyskinesia—between 1% and 5% depending on the population studied, the specific second-generation neuroleptic given, and the dose of the second-generation neuroleptic. (At higher dosages of some of the second generation neuroleptics, the dopamine receptor blocking action predominates over other neurotransmitter actions and its pharmacodynamic effect is essentially that of a first generation agent.) The second generation drugs, however, have a major problem—they frequently cause weight gain and glucose intolerance that can lead to frank diabetes and accelerated atherosclerosis, with significant impact on patients' life expectancy. Thus the second generation neuroleptics do not provide a safe alternative to first generation neuroleptics—simply an alternative with a lesser propensity to cause movement disorders. They are not in general more efficacious than first generation drugs in the treatment of schizophrenia, with the sole exception of clozapine, a drug with numerous other adverse effects including seizures and agranulocytosis that limit its clinical use.

Acamprosate can be used as a treatment for obsessive compulsive disorder (OCD), posttraumatic stress disorder (PTSD), and other neuropsychiatric conditions characterized by recurrent, involuntary, unwanted, and stereotyped movements, behaviors, thoughts, or perceptions—the symptoms of OCD and PTSD falling within that broader ambit. Serotonin reuptake inhibitors—both selective serotonin reuptake inhibitors and serotonin-norepinephrine reuptake inhibitors—can have therapeutic benefits in PTSD and OCD. Thus, some embodiments relate to the combination of acamprosate and an SSRI or SNRI. The fact that GR acamprosate formulations as described herein can be efficacious in total doses of less than 1 gram per day, given on a once-daily or twice-daily basis, makes such combinations feasible, which they were not heretofore when only enteric-coated acamprosate was available and therapeutic efficacy typically required 2 grams per day or more, entailing six or more enteric-coated tablets per day on a three times daily schedule.

Thus, some embodiments relate to combinations of GR acamprosate with either an SSRI or an SNRI. Examples of non-limiting amounts or dosages are provided herein. These combinations can be given once or twice daily, for example. Also, some embodiments relate to the treatment of neuropsychiatric conditions characterized by recurrent, involuntary, unwanted and stereotyped movements, behaviors, thoughts, or perceptions, and in particular PTSD and OCD.

Acamprosate when used to treat alcoholism is typically administered in 333-mg enteric-coated tablets. The dose is two tablets (666 mg) three times daily, for a total dose of approximately two grams. Doses of up to 3 grams (three tablets three times a day) have been studied as alcoholism treatment; the higher dose does not appear to be more effective and it has more gastrointestinal side effects. One reported study assessed the pharmacokinetics of acamprosate using liquid chromatography (Hammarberg, et al., "Acamprosate Determinations in Plasma and Cerebrospinal Fluid After Multiple Dosing Measured by Liquid Chromatography—Mass Spectroscopy: A Pharmacokinetic Study in Healthy Volunteers," *The Drug Monit*, 2010, 32:489-496). It showed that blood levels of acamprosate build up with repeated dosing, for example, 666 mg doses. The instant technology that can efficaciously provide sub 1 gram total daily doses is surprising and unexpected in view of such earlier studies.

When used to treat TD and other neuropsychiatric disorders it has been used at dosages ranging from 1 gm to 3.6 grams per day (3 to 11 tablets daily) on a thrice-daily schedule. The average dose for treating TD has been 3 grams daily. Prior to the instant technology, in general clinical practice no patient has had an optimal response on less than 2 grams per day.

The most common side effects of acamprosate are gastrointestinal symptoms—including nausea, vomiting, diarrhea, and dyspepsia. For patients with alcoholism these side effects often lead to noncompliance, and in turn to decreased effectiveness of treatment. For patients with TD, who often are so distressed by their movements that they will adhere to effective treatment despite side effects, the gastrointestinal side effects make treatment unpleasant, or limit the acamprosate dose to one that does not completely relieve their involuntary movements. For all patient groups taking multiple pills three times daily is inconvenient and burdensome.

The gastrointestinal side effects of acamprosate are thought to be due to the local irritation of the stomach and intestine by the drug, and not due to central effects of the acetylhomotaurinate ion in the blood. Thus, enhancing the bioavailability of oral acamprosate can reduce the gastrointestinal side effects without compromising its efficacy.

Some embodiments provided herein relate to alternative formulations of acamprosate that allow a smaller dose to be used, but that surprisingly and unpredictably have sufficient or equal efficacy. Such formulations can have greater bioavailability, for example, than the existing enteric-coated formulation.

Without being limited thereto, in some instances the greater therapeutic potency of the new oral formulations can come from changes in the drug's PK profile that allow the same therapeutic benefits to be obtained from a smaller total area under the time-concentration curve (AUC). Greater oral bioavailability, if it is attained, is an additional benefit that may enable even greater oral potency. However, what is surprising, unpredicted and unexpected here in some embodiments is the increase in therapeutic potency that is independent of any increase in oral bioavailability. Thus, in some embodiments, greater therapeutic potency of oral formulations can be attained by altering the pharmacokinetics (PK) of the drug to make it more efficacious despite a smaller AUC in the blood. In particular, some embodiments relate to formulations and dosage schedules that maintain the acamprosate concentration above a threshold for a sufficient time during each 24-hour day. Such formulations and schedules are efficacious even though the acamprosate concentration does not exceed the threshold for the entire 24 hour period.

There are at least several ways to reformulate drugs to alter their PK profiles according to the instant technology. The technology described here relates to the use of any of such formulation technologies to alter the PK profile of acamprosate in a way that makes it efficacious (including in some aspects, more efficacious) with a lower area under the curve than that produced by three times daily administration of the currently-marketed enteric-coated formulation. This in turn makes possible the administration of lower oral doses of acamprosate—less than one gram per day—on a less frequent schedule—once or twice daily—than has been described heretofore. The lower oral daily doses of acamprosate described herein are not necessarily bioequivalent to higher daily doses of enteric-coated acamprosate that have been previously shown efficacious for the various indications for the drug. In fact, in some embodiments the lower daily doses and once- or twice-daily schedule described for the new formulations usually will produce a lower total area under the curve (AUC) than the therapeutically equivalent doses of the enteric-coated preparation given three times a day, so their equal efficacy is an unexpected finding.

The technology according to some embodiments described herein is based on several original observations: (1) There are clinical cases in which giving the existing enteric-coated acamprosate to patients on a twice-daily schedule made a daily dose more efficacious than when given on a thrice-daily schedule. Thus, it has been discovered that the shape of the PK curve and not just the AUC can make a difference to efficacy. Specifically, that having a blood concentration above a threshold for several hours per day may be more efficacious than maintaining a concentration just below that threshold for 24 hours a day. (2) In a dog model of a GR controlled release system applicable to a wide range of GR and controlled release technologies it was shown (see EXAMPLE 3 below) that controlled presentation of acamprosate over eight hours yielded a significantly longer residence time above a threshold concentration than immediate release of the same dosage, even when there was not a significant decrease in the AUC. In the model of controlled release, the drug "saved" by avoiding a high $C_{max}$ was distributed across several hours, giving a several hour period in which the blood concentration of acamprosate was higher than the blood concentration after administration of a single dose of the immediate release version. (3) Clinical observations of TD cases where enteric coated acamprosate given three times daily had greater efficacy at a given daily dosage when the daily dosage was divided unevenly among the three doses. (4) The therapeutic action of acamprosate in TD is based on its effects on glutamate transmission. These effects are not based on direct interaction of acamprosate with glutamate receptors, but rather on downstream effects of acamprosate modulation at other sites on the neuron. These downstream effects are based in part on modulation of RNA transcription, a mechanism implying the potential for persistence of effect after the drug is no longer present at a threshold level for clinical efficacy.

Further, a controlled release GR version of acamprosate can cause significantly less GI side effects than the immediate-release version, since the maximum concentration of the drug in the gastric juice or in the intestine will be lower than with the immediate release version.

It is known that immediate release acamprosate (which is equivalent to acamprosate solution because acamprosate is immediately and completely soluble in gastric juice) has twice the bioavailability as enteric-coated acamprosate (Saivin S et al., Clinical Pharmacokinetics of Acamprosate, Clinical Pharmacokinetics Vol. 35, Number 5, November 1998, pp. 331-345, which is incorporated herein by reference in its entirety). The new observations and discoveries reported here demonstrate that controlled release acamprosate delivered by a GR system can be at least 50% more potent than IR acamprosate for treating TD and other neuropsychiatric disorders. Thus, controlled release GR formulations can be efficacious at total daily doses of less than 1 gram per day, and these formulations can be given on a twice-daily schedule, and even on a once-daily schedule, depending on the threshold blood level and daily time above that level required for efficacy in a given patient. The model system studied was based on gastric retention and controlled release over eight hours. It is evident that GR and controlled release over six hours or controlled release over four hours can be satisfactory for therapeutic advantage, depending on the time and concentration thresholds for efficacy in particular patient populations and for particular indications.

The dog study of simulated GR acamprosate (EXAMPLE 3 below) showed that comparing the PK curve (time×plasma concentration curve) for simulated GR acamprosate (intragastric administration of IR acamprosate every half hour in amounts that decrease linearly with the square root of time) with the PK curve for intra-gastric administration of the same total dose of IR acamprosate all at once, the curve for simulated GR acamprosate lies above the curve for IR acamprosate for more than six hours (see PK plots from the dog study). Thus, the time above critical threshold is hours greater for simulated GR acamprosate than for IR acamprosate, for a significant range of values for the critical threshold. Furthermore, the area under the curve (AUC) for GR acamprosate usually is greater than the AUC for IR acamprosate—and sometimes significantly greater.

Enteric-coated acamprosate is only half as bioavailable as IR acamprosate and has a lower maximum concentration ($C_{max}$) and longer time to peak concentration ($T_{max}$) than IR acamprosate. GR acamprosate has an even greater therapeutic advantage over enteric-coated acamprosate than over IR acamprosate. Furthermore, the steady-state concentration in the blood when enteric-coated acamprosate is given three times a day is approached slowly over 5-7 days, with the plasma level of acamprosate during the first several days of administration below the eventual steady-state plasma level. By contrast, a gastric retentive formulation of acamprosate according to embodiments described herein that provides controlled delivery of acamprosate into the stomach and thence the duodenum—with a single dose can reach the blood level of acamprosate attained only after several days on the enteric-coated version, and it might maintain that level for several hours. One or two doses daily of the acamprosate formulations described herein can be efficacious even though the daily AUC might lie below the daily AUC for enteric-coated acamprosate dosed three times a day on an ongoing basis.

GR formulations of acamprosate can produce a PK curve almost identical to that of simulated GR acamprosate if that formulation releases acamprosate into gastric juice at a rate proportional to the square root of time. Some embodiments herein relate to the use of any GR formulation that releases acamprosate at such a rate (or close to it). One non-limiting example of a specific GR formulation described herein (see EXAMPLE 6 below) does release acamprosate at such a rate (see for example the tables showing the composition of the 400 mg and 800 mg GR acamprosate tablets tested; see the in vitro drug release data in two different media—one highly acidic and typical of fasting gastric juice and the other with a pH typical of gastric juice in the fed state). The PK curve of such GR acamprosate in dogs (and in humans) lies above the PK curve for the same dose of IR acamprosate or of enteric-coated acamprosate for several hours.

GR acamprosate can be more than twice as bioavailable as enteric-coated acamprosate. Thus, less than 1.3 gm per day of GR acamprosate can have the therapeutic effect of 2.6 gm of enteric-coated acamprosate, the latter being the upper limit of dose ranges for acamprosate in the treatment of TD and other neuropsychiatric disorders described in previously issued patents. Thus, dosing of GR acamprosate at 400 mg three times a day can give therapeutic results equivalent to 2.6 gm per day of enteric coated acamprosate.

However, consistent with the human case set forth in EXAMPLE 1 that evidences that there is a therapeutic threshold that need be exceeded for significantly less than 24 hours, for example, eight hours per 24 hours, the dosing of 400 mg of GR acamprosate twice a day, or possibly 800 mg once a day, can be effective. This results in the total acamprosate dose for the GR formulation being below 1 gm per day—less than the previously recognized therapeutic range—even for a case that would require 2.6 gm per day of the enteric-coated formulation for efficacy, in a situation where the GR formulation at that dose did not produce as high an AUC as 2.6 gm of the enteric-coated formulation.

Further, it should be understood that according to some embodiments the sub gram, twice or once a day regimens (e.g., 400 mg twice a day or 800 mg once a day regimens) of GR acamprosate do not give equivalent concentrations in the blood to those produced by enteric-coated acamprosate given in a higher total daily dose on a three times daily schedule. The latter would give—after 5-7 days—a stable level of acamprosate, whereas the GR regimens can produce a fluctuating level of acamprosate that might be below the steady state level for enteric-coated acamprosate, at some times of the day. Thus, the GR formulation given at less than 1 gm per day would not necessarily be bio-equivalent to the enteric-coated formulation given at dosages of 1 gm to 2.6 gm on a three times a day schedule, and in fact it can even have a lower total AUC in 24 hours than that produced by 2.6 grams daily of acamprosate. For these reasons the use of GR acamprosate at a daily dose of less than 1 gm per day given on a once-daily or twice-daily basis is not suggested by the prior art, and its efficacy for TD (and for other neuropsychiatric disorders) is a novel and unexpected discovery.

The GR acamprosate formulations (e.g., tablets) according to some embodiments herein can thus be of size such that the total tablet or pill is easy to swallow. For example, the specifically described formulations herein, in particular, 400 mg GR acamprosate tablets and even 800 GR acamprosate tablets are small enough to be easily swallowed. They thus make possible reasonably-sized fixed-dose combination tablets comprising GR acamprosate and another drug that is given in a lower dosage than the GR acamprosate. In some embodiments these formulations are novel compositions because they are made feasible by the reduction in daily acamprosate dose and dosage frequency made possible by the GR formulation of acamprosate and the finding that a threshold level of acamprosate need not be maintained for 24 hours per day for efficacy.

Some embodiments of the present technology introduce a way to administer a therapeutic dosage of acamprosate in one (relatively) small dose that only has to be taken once or twice daily. The smaller dosage form also can have ancillary benefits. First of all, the smaller dosage can lead to lesser side-effects. It also can lead to improved patient compliance due to being taken fewer times each day, for example, once daily. Additionally, smaller dosage forms allow for more convenient co-administration of acamprosate with other drugs, for example as part of a single dosage form or as separate dosage forms.

Acamprosate Formulations

Some embodiments relate to formulations comprising acamprosate designed for sustained or controlled release. Examples of sustained or controlled release pharmaceutical formulations that can be used with acamprosate include, for example, the materials and methods described in U.S. Pat. Nos. 3,536,809; 3,598,123; 3,845,770; 3,916,899; 4,008,719; 4,404,183 4,690,820; 4,851,232; 4,861,598; 4,871,548; 4,970,075; 4,992,278; 5,007,790; 5,059,595; 5,073,543; 5,120,548; 5,273,758; 5,354,556; 5,458,887; 5,582,837; 5,591,767; 5,674,533; 5,718,700; 5,733,566; 5,736,159; 5,783,212; 5,840,754; 5,912,268; 5,972,389; 6,120,803; 6,340,475; 6,365,183; 6,403,120; 6,451,808; 6,488,962; 6,548,083; 6,635,280; 6,635,281; 6,682,759; 6,723,340; 6,797,283; 7,405,238; 7,413,751; 7,438,927; 7,514,100; 7,612,112; 7,731,989; Re.34,990; U.S. Pat. No. 7,736,667; and U.S. Pat. No. 7,976,870; U.S. Patent Pub Nos. 20110091542; 20090304768; 20090304753; foreign patent publication numbers EP 0,661,045, A1; JP Kokei 61233632 and PCT publication numbers WO 9929297; WO 9912527; WO 9930692; WO 9921551; WO 9929305, WO 9917745; WO 9906045, WO 9833489; WO 9855107; WO 9811879; WO 9815264; WO 9737640; WO 9733566; WO 9748385; WO 9747285; WO 9718814; WO 9637202; WO 9637189; WO 9613248; WO 9608253; WO 9600065; WO 9626718; WO 9626717; WO 9632097; WO 9529665; WO 9519174; WO 9,591,174; WO 9530422; WO 9427587; WO 9625153; each of which is incorporated herein by reference in its entirety. In each of the listed patents and publications, acamprosate in a dosage of less than 1 gram (e.g., 100 mg to 900 mg) can be used as an active agent replacing or in addition to other agents described in the respective document using the particular formulation technology that is described, for example. In particular, the U.S. Pat. No. 7,514,100 patent provides a description regarding how to incorporate various technologies to obtain extended release formulations, and the description can be used for acamprosate formulations.

Some embodiments disclosed herein relate to pharmaceutical dosage forms comprising gastroretentive controlled release acamprosate at a specified dosage in combination with a first generation neuroleptic or metoclopramide at a specified dosage, with a second generation neuroleptic at a specified dosage, or with a serotonin reuptake inhibitor (SSRI or SNRI drug) at a specified dosage.

Active Agent

The controlled release oral dosage forms of the present technology preferably include less than 1 gram (e.g., from about 50 mg to 900 mg) acamprosate or an equivalent amount of a pharmaceutically acceptable salt thereof, such as for example the magnesium, sodium, or lithium salt. For example, the dosage can be 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg or any value or sub range within that larger range. As noted elsewhere herein, other salts are contemplated, as are analogs of acamprosate and salts thereof.

If a second drug is included in the formulation, such drug may be included in controlled release form or in immediate release form. The additional drug may be incorporated into the matrix (e.g., controlled release matrix) along with the acamprosate; incorporated into a coating (e.g., a controlled release coating); incorporated as a separate band or layer (e.g., a separated controlled release layer or immediate release layer); or may be incorporated as a powder, granulation, etc., in a gelatin capsule with the substrates.

Dosage Forms

The controlled-release dosage form may optionally include a controlled release material which is incorporated into a matrix along with the acamprosate, or which is applied as a sustained release coating over a substrate comprising the drug (the term "substrate" encompassing beads, pellets, spheroids, tablets, tablet cores, etc.). The controlled release material may be hydrophobic or hydrophilic as desired. The oral dosage form may be provided as, for example, granules, spheroids, pellets or other multi particulate formulations. An amount of the multi particulates which is effective to provide the desired dose of acamprosate over time may be placed in a capsule or may be incorporated in any other suitable oral solid form, e.g., compressed into a tablet. On the other hand, the oral dosage form may be prepared as a tablet core coated with a controlled-release coating, or as a tablet comprising a matrix of drug and controlled release material, and optionally other pharmaceutically desirable ingredients (e.g., diluents, binders, colorants, lubricants, etc.). The controlled release dosage form may also be prepared as a bead formulation or an osmotic dosage formulation.

Controlled Release Matrix Formulations

U.S. Pat. No. 7,514,100 (the '100 patent) describes in detail methods of achieving controlled release formulations in dosages of drugs and is included by reference, herein. The '100 patent explains how to achieve a controlled-release formulation via a matrix which includes a controlled release material—either a hydrophilic or hydrophobic material.

Controlled release can be accomplished by (a) forming granules comprising at least one hydrophobic and/or hydrophilic material (e.g., a water soluble hydroxyalkyl cellulose) together with the acamprosate; (b) mixing the at least one hydrophobic and/or hydrophilic material containing granules with at least one $C_{12}$-$C_{36}$ aliphatic alcohol, and (c) optionally, compressing and shaping the granules.

The matrices can also be prepared via melt pelletization, melt-granulation, or melt-extrusion techniques. The controlled release matrix may also contain suitable quantities of other materials, e.g., diluents, lubricants, binders, granulating aids, colorants, flavorants and glidants that are conventional in the pharmaceutical art in amounts up to about 50% by weight of the particulate if desired. It may also include combinations of multi-particulates containing one or more dyskinesia treatments or cures.

In certain embodiments, a spheronising agent can be added to a granulate or to multi particulates and then spheronized to produce controlled release spheroids. The spheroids are then optionally over coated with a controlled release coating by methods such as those described herein.

Preparation of Coated Bead Formulations

The '100 patent also explains that the oral solid controlled release dosage form can comprise a plurality of coated substrates. An aqueous dispersion of hydrophobic material is used to coat the beads to provide for the controlled release of the acamprosate. The stabilized controlled-release bead formulations slowly release the acamprosate, e.g., when ingested and exposed to preferably to gastric fluids, but also to intestinal fluids. Substrates coated with a therapeutically active agent are prepared, e.g. by dissolving the therapeutically active agent in water and then spraying the solution onto a substrate.

Controlled Release Osmotic Dosage

Controlled release dosage forms may also be prepared as osmotic dosage formulations.

Coatings

The dosage forms as described herein may optionally be coated with one or more coatings suitable for the regulation of release or for the protection of the formulation. For instance, a coating can be added that provides for either pH-dependent or pH-independent release, e.g., when exposed to gastrointestinal fluid. When a pH-independent coating is desired, the coating is designed to achieve optimal release regardless of pH-changes in the environmental fluid, e.g., the GI tract. Other preferred embodiments include a pH-dependent coating that releases the acamprosate in desired areas of the gastrointestinal (GI) tract, e.g., the stomach or small intestine. It is also possible to formulate compositions which release a portion of the dose in one desired area of the GI tract, e.g., the stomach, and release the remainder of the dose in another area of the GI tract, e.g., the small intestine.

Alkylcellulose Polymers

Cellulosic materials and polymers, including alkylcelluloses are controlled release materials well suited for coating the substrates, e.g., beads, tablets, etc.

Alkylcellulose Polymers

Cellulosic materials and polymers, including alkylcelluloses are controlled release materials well suited for coating the substrates, e.g., beads, tablets, etc.

Acrylic Polymers

In other preferred embodiments, the controlled release material comprising the controlled-release coating is a pharmaceutically acceptable acrylic polymer.

Plasticizers

In embodiments where the coating comprises an aqueous dispersion of a hydrophobic controlled release material, the inclusion of an effective amount of a plasticizer in the aqueous dispersion of hydrophobic material will further improve the physical properties of the controlled-release coating.

The controlled-release coatings may also include an exit means comprising at least one passageway, orifice, or the like. The passageway may be formed by such methods as those disclosed in U.S. Pat. Nos. 3,845,770; 3,916,889; 4,063,064; and 4,088,864; each of which is incorporated herein by reference in its entirety. The passageway can have any shape such as round, triangular, square, elliptical, irregular, etc.

Since acamprosate is absorbed in the intestinal tract, controlled release of the drug preferably entails or in some cases may require, among other things, that the drug dosage form be maintained in the stomach for a number of hours. Without any modifications, the transit time of an oral dosage form in the stomach is less than three hours. Wen H, Park, K Oral Controlled Release Formulation Design and Drug Delivery: Theory to Practice.) Therefore, a preferred method of accomplishing controlled release is to deliver it with a gastroretentive drug dosage system. Several approaches to gastroretentive drug dosage systems are described in Surana A S, Kotecha R K An Overview on Various Approaches to Oral Controlled Drug Delivery System Via Gastroretention. Int'l. J. Pharm. Sci. Rev. and Research 2010; 2:68-72 and U.S. Pat. App. 2005/0249798, now abandoned; each of which is incorporated herein by reference in its entirety.

The first (and most common) is a floating drug delivery system, which works by using a low density system so that the drug-containing system has sufficient buoyancy to float over the gastric contents and remains in the stomach for a prolonged period. There are two ways to make a buoyant system. The first is an effervescent system and the second is a non-effervescent system.

In effervescent systems the buoyancy is achieved by using swellable polymers such as METHOCEL® or polysaccharides, and effervescent components or liquids that gasify at body temperature. When the system reaches the stomach gas is released into the polymers—e.g. because reaction in the strongly acidic stomach causes gas release or because a liquid gasifies at body temperature-and this maintains the system's buoyancy. Such methods are described, e.g., in U.S. Pat. Nos. 3,901,232, 3,944,064, 4,996,058, 5,651,985 and German Offenlegungsschrift (DE-A) No. 3,527,852; each of which is incorporated herein by reference in its entirety. The very same material that swells can also be one that slowly erodes, thus delivering a controlled release system.

In non-effervescent systems a high level of gel-forming, highly swellable, cellulosic hydrocolloids, polysaccharides, or matrix-forming polymers are used. When they reach the stomach the compounds "hydrate and form a colloidal gel barrier that controls the rate of fluid penetration into the device and consequent drug release." The trapped air confers buoyancy. As the exterior of the drug delivery device dissolves, the interior swells, thus maintaining the buoyancy. The slow erosion can also be used to deliver a controlled release of the drug. Hydrophilic polymers that swell upon intake of water from gastric fluids have been previously described, for example, U.S. Pat. Nos. 6,723,340, 6,488,962, 6,340,475 and 6,635,280; each of which is incorporated herein by reference in its entirety. These patents disclose systems wherein the dosage form swells to a size large enough that it remains in the stomach because it cannot pass through the pyloric sphincter when the sphincter is contracted, such as in the fed mode. As a result, the dosage remains in the stomach for at least four hours. These formulations may be designed to produce desired release and delivery profiles for both highly soluble and poorly soluble drugs.

The second system is a bio/mucoadhesive system, which works by using a substance that binds to the gastric mucosa (either to mucous cell membranes or to the mucus secreted by them), thus increasing the system's residence in the stomach. Bioadhesive polymers bind either to the membranes; mucoadhesive polymers bind to the mucus lining.

In some embodiments, the characteristics of these polymers are, for example, molecular flexibility, hydrophilic functional groups, and specific molecular weight, chain length, and conformation. Furthermore, in some embodiments, they can be nontoxic and nonabsorbable, can form noncovalent bonds with the mucin-epithelial surfaces, can have quick adherence to moist surfaces, can easily incorporate the drug and offer no hindrance to drug release, and have a specific site of attachment, for example.

There are three broad categories of bio/mucoadhesive systems: hydration-mediated adhesion, bonding-mediated adhesion and receptor-mediated adhesion.

In hydration-mediated adhesion, the binding substance is a swellable polymer that absorbs large amounts of water and therefore becomes sticky. Bonding-mediated adhesion is achieved either through physical or chemical binding. In physical binding the adhesive material inserts into crevices or folds of the mucosa. In chemical bonding the binding substance forms chemical bonds (either covalent, ionic, or hydrogen bonds or van der Waals interactions). Finally, in receptor mediated adhesion the binding substance directly binds to specific receptor cells in the mucus or the gastrointestinal tract. For instance, certain plant lectins bind sugar groups present in the mucus or on the glycocalyx. These can be combined with ion exchange resins. (Burton S; Washington N; Steele R J C; Musson R; Feely L, J. Phar. Pharm. 47, 901; which is incorporated herein by reference in its entirety.)

A third method to obtain gastroretentive drug dosage systems is to use a swelling/expanding system where the dosage form swells so that it cannot pass through the pylorus, and is consequently stuck in the stomach. The swelling can be obtained by using a polymer that swells when in contact with water, but that has crosslinks in the hydrophilic polymer network to prevent the dosage form from coming apart and dissolving. A balance between the extent and the duration of the swelling is achieved by selecting the amount of cross linking. If there are many crosslinks, the system will swell poorly but last for a long time. Conversely, if there are few crosslinks, the system will swell will but will dissolve more rapidly. Eventually, the system will dissolve either because of interactions with the gastric juice or because of abrasion with other particles in the stomach. Such swelling mechanisms are described, e.g., in U.S. Pat. Nos. 3,574,820, 4,207,890, 4,434,153, 4,767, 727, 4,735,804, 4,758,436, 5,002,772, 5,047,464, 5,217,712, 5,443,843, 5,651,985, 6,685,962, 7,736,667, 7,976,870 and German Pat. No. 2,328,580; each of which is incorporated herein by reference in its entirety. A similar approach is suggested by U.S. Pat. App. 2005/0249798, now abandoned, and U.S. Pat. Apps. 2009/0304753 and 20090304768; each of which is incorporated herein by reference in its entirety; wherein the drug device is a folded sheet that unfolds (in some embodiments like an opening accordion) when it swells. The very same material that swells can also be one that slowly erodes, thus delivering a controlled release system if the drug is distributed throughout the pill.

A fourth approach is to use a high density dosage form where the drug dosage form sinks to the bottom of the stomach and is entrapped in the stomach folds, thus allowing it to withstand the peristaltic waves of the stomach wall. Examples of high density components that are added to obtain high density drug dosage forms are barium sulphate, zinc oxide, iron powder, and titanium dioxide.

The final approach is a magnetic system. The drug is administered with a small internal magnet or magnetizable element. An external magnet is placed over the stomach thus preventing the drug dosage form from travelling past the stomach.

Using one of these methods for achieving gastric retention of the drug delivery system, it next can be necessary to achieve controlled release of the active pharmaceutical ingredient. There are a number of potential methods; these are reviewed in the monograph Wen H, Park, K Oral Controlled Release Formulation Design and Drug Delivery: Theory to Practice, which is incorporated herein by reference in its entirety.

The first method is to use dissolution-controlled formulations. One approach is the encapsulated dissolution system where a system comprised of many small beads is coated with a dissolvable material, such as a polymer. The beads are of varying thickness, so that the outer layers of the various beads dissolve at different times (because of the different thicknesses among the beads). The beads can be compressed into tablets or filled into capsules. Alternatively, a matrix dissolution system can be used, wherein the drug is homogenously distributed throughout the polymer matrix. As the polymer dissolves, the drug trapped in that part of the polymer is released.

The second method is diffusion-controlled formulations, where the drug has to diffuse through a polymer membrane or matrix to be released. The first approach to diffusion-controlled formulations is a reservoir system, wherein the drug is surrounded by a polymer membrane. Alternatively, a monolithic system can be used, wherein the drug is distributed through the polymer matrix.

A third method is osmosis-based formulations, wherein the drug is surrounded with a semi permeable membrane, such as cellulose acetate, with at least one small orifice. Only water can diffuse through the membrane, so the concentration of water in the dosage form increases and the drug, dissolved in the water, seeps out of the orifice at a controlled rate.

A fourth method is ion exchange-based formulations, wherein the drug is ionically bound to an ion-exchange resin that is water-insoluble. The drug is released when other ions with the same charge bind the resin. Finally, some of these methods can be combined. For instance, it is possible to cover an ion-exchange resin with a diffusion controlled formulation.

The PK of acamprosate delivered by any of these formulations can be expected to be similar to that produced by the administration of IR capsules containing a fraction of the total dose, on a periodic basis at intervals of 30 minutes or less. Thus, the procedure used in the dog PK study reported herein can be a model for the PK to be obtained from any of the formulations described here.

Acamprosate delivered by a GR system can be efficacious for treating tardive dyskinesia and other neuropsychiatric indications if it is given at a dose sufficient to give blood concentrations greater than or equal than those produced by an effective dose of the currently-marketed enteric-coated preparation. A dose and dosing schedule cannot be assumed a priori to be efficacious if it does not produce equal or greater concentrations.

Two clinical cases demonstrate that the efficacy of acamprosate for its neuropsychiatric indications can depend on having an adequate blood level of the drug for substantially less than 24 hours a day. As such, GR preparations of acamprosate capable of maintaining a blood level above a target concentration for 8 hours a day can be effective given once or at most twice a day. Now, the AUC for IR acamprosate in humans is twice the AUC for the currently-marked enteric-coated acamprosate utilized in the cases described in previous patents on neuropsychiatric uses of acamprosate, and the AUC for the same dose of GR acamprosate can be at least as high as that—and perhaps higher in some cases, as shown in the dog study PK study described herein conducted by the inventors. The case shows that if an effective dose of acamprosate is divided into three equal parts, then one or two of those parts will suffice to treat the disorder if they are formulated as a GR controlled-release system that deliver the dose over eight hours in a manner that produces an essentially flat time-concentration curve. If so, less than one-third of the dose given using the currently-marketed enteric-coated version can have the same efficacy. The dosage range specified to date for treating neuropsychiatric disorders with enteric-coated acamprosate is 1 to 2.6 grams. The above considerations show efficacy with a daily dose of GR acamprosate of less than 1 gram per day given on a once or twice per day basis. An efficacious dose can potentially be as low as 100 mg once a day, if in a given case 1 gram per day of the enteric-coated formulation is efficacious and a single daily dose of the GR formulation that was ⅓ of the total daily dose was efficacious, and overall bioavailability of the GR formulation was 40% higher than with an IR formulation (a number within the range suggested by the dog study reported herein.

Any of the foregoing mixtures and compositions can be appropriate in treatments and therapies in accordance with the invention disclosed herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J Pharm Sci 0.89(8):967-78 (2000), and the citations therein for additional information related to formulations, excipients and carriers well known to pharmaceutical chemists.

As noted herein the formulations can include various materials. Among such materials are fillers. In some embodiments, the compositions can include one or more fillers, for example, microcrystalline cellulose, lactose, a compressible sugar, xylitol, sorbitol, mannitol, pregelatinized starch, maltodextrin, calcium phosphate dibasic, calcium phosphate tribasic, calcium carbonate DC, a calcium silicate, a combinations of one or more of the same, or the like. In one aspect of this embodiment, the at least one filler can be microcrystalline cellulose. The microcrystalline cellulose (other filler or combination of fillers) can be provided in an amount of about 8% to about 90% w/w. The precise amount can depend upon the amount of the acamprosate and/or the amounts of other excipients or materials, for example. The compositions can further comprise at least one of the following second fillers, lactose, compressible sugars, xylitol, sorbitol, mannitol, pregelatinized starch, maltodextrin, calcium phosphate dibasic, calcium phosphate tribasic, calcium carbonate DC, a combinations of one or more of the same, or the like.

Any other suitable excipient(s) may be used in the formulation. For example, excipients suitable for use include, but are not limited to, binders, diluents, disintegrants, lubricants, fillers, carriers, and the like.

In one embodiment, the formulation comprises a mixture of the acamprosate in a gastric retentive and/or controlled release formulation. Such formulations can include any of the substances described herein, and additional processing aides, such as, for example, magnesium stearate and colloidal silicon dioxide, and optionally, colorant(s). For example, in some embodiments, colloidal silicon dioxide, may be added separately to the formulation as a glidant. Without being limited thereto, colloidal silicon dioxide can be added at concentrations ranging from about 0.1% to about 5.0% w/w, or from about 0.25% to about 2% w/w, or from about 0.5% to about 1% w/w.

In some embodiments, magnesium stearate can be added as a lubricant, for example, to improve powder flow, prevent the blend from adhering to tableting equipment and punch surfaces and provide lubrication to allow tablets to be cleanly ejected from tablet dies. Magnesium stearate can typically be added to pharmaceutical formulations at concentrations ranging from about 0.1% to about 5.0% w/w, or from about 0.25% to about 2% w/w, or from about 0.5% to about 1.25% w/w.

In some embodiments, color additives also can be included. The colorants can be used in amounts sufficient to distinguish dosage form strengths. Preferably, color additives approved for use in drugs (21 CFR 74, which is incorporated herein by reference in its entirety) are added to the commercial formulations to differentiate tablet strengths. The use of other pharmaceutically acceptable colorants and combinations thereof are encompassed by the current invention.

Binders can be used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, cellulosic polymers (including, for example, hydroxypropyl cellulose, hydroxypropyl methylcellulose, methyl cellulose, hydroxyethyl cellulose, and the like).

One of ordinary skill in the art would recognize additional binders and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of binder added in order to keep the overall unit weight of the tablet unchanged. In one embodiment, the binder(s) is(are) sprayed on from solution, e.g. wet granulation, to increase binding activity.

Disintegrants can be used, for example, to facilitate tablet disintegration after administration, and are generally starches, clays, celluloses, algins, gums or crosslinked polymers. Suitable disintegrants include, but are not limited to, crosslinked polyvinylpyrrolidone (PVP-XL), sodium starch glycolate, and croscarmellose sodium. If desired, the pharmaceutical formulation can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc. and the like. One of ordinary skill in the art would recognize additional disintegrants and/or amounts of disintegrants that can be used in the formulations described herein. As would be recognized by one of ordinary skill in the art, when incorporated into the formulations disclosed herein, the amounts of the major filler(s) and/or other excipients can be reduced accordingly to accommodate the amount of disintegrant added in order to keep the overall unit weight of the tablet unchanged.

In some embodiments, the formulations can include a coating, for example, a film coating. Where film coatings are involved, coating preparations can include, for example, a film-forming polymer, a plasticizer, or the like. Also, the coatings can include pigments and/or opacifiers. Non-limiting examples of film-forming polymers include hydroxypropyl methylcellulose, hydroxypropyl cellulose, methylcellulose, polyvinyl pyrrolidine, and starches. Non-limiting examples of plasticizers include polyethylene glycol, tributyl citrate, dibutyl sebecate, castor oil, and acetylated monoglyceride. Furthermore, non-limiting examples of pigments and opacifiers include iron oxides of various colors, lake dyes of many colors, titanium dioxide, and the like.

One can also prepare or administer the compounds of the invention in sustained-release forms or from sustained-release drug delivery systems. A description of representative sustained release materials can be found in the incorporated materials in *Remington: The Science and Practice of Pharmacy* (20$^{th}$ ed, Lippincott Williams & Wilkens Publishers (2003)), which is incorporated herein by reference in its entirety.

A variety of techniques for formulation and administration can be found in *Remington: The Science and Practice of Pharmacy* (20$^{th}$ ed, Lippincott Williams & Wilkens Publishers (2003)), which is incorporated herein by reference in its entirety.

As mentioned above, the compositions and formulations disclosed herein also can include one or more pharmaceutically-acceptable carrier materials or excipients. Such compositions can be prepared for storage and for subsequent administration. Any acceptable carriers or diluents for therapeutic use can be used, including those described, for example, in the incorporated material of *Remington: The Science and Practice of Pharmacy* (2003), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, and semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants. Sterile compositions for injection can be formulated according to conventional pharmaceutical practice as described in the incorporated material in *Remington: The Science and Practice of Pharmacy* (2003). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The compound can also be made in microencapsulated form. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

Enhancement of Gastric Retention Using Fed Mode Inducing Agent

Gastric retentive drug delivery systems can have improved function when the patient is in the fed mode, when the stomach does not produce the intense peristaltic contractions of Phase III of the Migrating Motor Complex (MMC). However, food can diminish the bioavailability of acamprosate by approximately 30%. Without intending to be bound by theory, although the mechanism of the food effect on acamprosate bioavailability is unknown, it is likely to be related to competition for a passive transport mechanism of limited capacity. The inventors have determined that for even more optimal pharmacokinetics and bioavailability of acamprosate, the fed mode can be induced affecting the MMC without interfering with the absorption of acamprosate in the way that a full meal would.

Accordingly, in some embodiments, an agent is co-administered with acamprosate to induce a "fed mode" in the stomach, inhibiting contractions of the MMC and increasing gastric retention time. In some embodiments, the fed mode inducing agent is any suitable fed mode inducing agent, including without being limited thereto any of those described in U.S. Pat. No. 7,405,238, the content of which is incorporated herein by reference in its entirety. For example, the fed mode inducing agent can be an agent selected from the group consisting of one or more of: (a) glycine, glycylglycine, and salts of either of these two compounds (b) C4-C8 sugar alcohols (c) alkali and alkaline earth metal docusates (d) beta-casomorphins (e) dithioorganic acids such as alpha-lipoic acid (racemic mixtures, enantiomers such as the R enantiomer, or enriched enantiomeric mixtures). In typical embodiments, the fed mode inducing agent is alpha-lipoic acid, for example. In some embodiments, alpha-lipoic acid can be administered in a dosage of about 40 mg to 700 mg or any value or sub range there between. For example, 40, 50, 60, 70, 80, 90, 100, 120, 130, 140, 150, 160, 170, 180, 190, 200, 210, 220, 230, 240, 250, 260, 270, 280, 290, 300, 310, 320, 330, 340, 350, 360, 370, 380 390, 400, 450, 500, 550 to about 600 mg, or any value or sub range there between. In some aspects, the alpha-lipoic acid is in a dosage of from about 100 to about 300 mg, for example, or any value or sub range there between. In some aspects, the alpha-lipoic acid is given in its racemic form; in other aspects it is given as its R enantiomer. In some aspects, the alpha-lipoic acid is included in a gastric-retentive composition. In some aspects, the alpha-lipoic acid is at least partially in the coating of the gastric-retentive system. In some aspects, the alpha-lipoic acid is incorporated into a gastric-retentive system. In some aspects, the gastric-retentive system is designed to release the alpha-lipoic acid within a desired period of time, for example, the first hour after ingestion or any time period within the first hour, for example. In some aspects, alpha-lipoic acid is included in combination with acamprosate, for example, acamprosate in a dose of less than 1 gram (e.g., of 100 to 700 mg), or any value or sub range there between. In some aspects, alpha-lipoic acid is included in combination with acamprosate and further in combination with a neuroleptic (antipsychotic) drug. In some aspects, alpha-lipoic acid is included in combination with acamprosate and a serotonin reuptake inhibitor drug (SSRI or SNRI).

As exemplified in EXAMPLE 10 below, and as taught in the incorporated materials of U.S. Pat. No. 7,405,238, any suitable fed mode inducing agent can be utilized as an immediate-release coating of a gastric-retentive tablet. While not intending to be bound by theory, it is believed that when a fed mode inducing agent such as alpha-lipoic acid is incorporated into an immediate-release coating of a gastric-retentive tablet containing acamprosate, almost all of the alpha-lipoic acid would pass through the duodenum hours before most of the acamprosate would reach the duodenum; therefore it would be expected that little or no reduction in acamprosate bioavailability would occur, even if alpha-lipoic acid and acamprosate potentially compete for the same limited-capacity passive transport system. (In fact it is not known whether there is a common transporter.).

A dosage of alpha-lipoic acid in the range of about 40 mg to about 600 mg, about 60 mg to about 500 mg, about 80 mg to about 400 mg, or about 100 to about 300 mg (or any value or sub range there between any of those ranges and values) can be suitable when used as an immediate release component of a gastric retentive acamprosate tablet. For example, when alpha-lipoic is incorporated as a coating for the tablet, such a formulation can allow the patient to enjoy the pharmacokinetic benefits of GR acamprosate while taking the pill on an empty stomach.

As a non-limiting example, a GR acamprosate tablet can contain 350 mg of acamprosate in a swellable matrix, coated with mixture of inert ingredients and 150 mg of R-alpha-lipoic acid. Two such tablets taken, for example, once a day can provide the same therapeutic benefit as two to three grams of enteric-coated acamprosate tablets (6 to 9 pills, taken on a thrice-daily schedule), in the treatment tardive dyskinesia or other neuropsychiatric disorders. The two pills could be taken at bedtime or on awakening; thus the patient would take the medication, for example, once daily, at home. This schedule can greatly enhance convenience and treatment adherence.

For example, in the case of alcoholism treatment, strict compliance with treatment can be especially critical. Thus, the instant methods and compositions, which can provide greater convenience, ease of use, and compliance can result in better treatment for such patients. In fact, some embodiments of the technology described herein relate to methods and compositions for the treatment of alcohol dependence. The acamprosate can be formulated as set forth herein in a dosage as set forth herein. For example, the dosage can be up to 2-3 grams per day, but in some embodiments when formulated as described herein, it can be less than one gram per day, for example 40-700 mg or any subvalue or sub range therein. The improved adherence and/or convenience can be true and applicable for other conditions regardless of whether compliance is as important as in the case of treating alcohol dependence. The fact that the methods and compositions can provide improved convenience and compliance can be beneficial to many conditions that can be treated with acamprosate.

Other nutrients and drugs, including many described in the specification for U.S. Pat. No. 7,405,238 (incorporated herein in its entirety), can be used in place of alpha-lipoic acid. In particular embodiments, alpha-lipoic acid is used as the fed mode inducing agent. For example, alpha-lipoic acid is very safe. Second, the metabolic effects of alpha-lipoic acid can be of specific benefit in mitigating the side effects of antipsychotic drugs. Alpha-lipoic acid is an antioxidant, and oxidative stress is one of the mechanisms of neuroleptic-induced cellular damage to the basal ganglia that can cause TD. Additionally, alpha-lipoic acid has hypoglycemic actions that can mitigate the potential adverse effects of neuroleptics on glucose metabolism.

EXAMPLES

Example 1

Case 1: A 56-year old woman had long-standing tardive dyskinesia induced by treatment of schizoaffective disorder with a variety of neuroleptics and mood stabilizers. Her TD was characterized by side to side movements of the jaw, grimacing movements, rocking of the trunk, and continual involuntary kicking, leg-crossing, and twisting movements of her legs and feet. At the time she presented for treatment of her TD she was treated for her mental illness with lamotrigine and quetiapine, a second-generation neuroleptic. She was started on acamprosate 666 mg three times a day, with partial relief of symptoms. When acamprosate was increased to 999 mg three times a day she had complete relief of her TD. After two months free of symptoms of TD she switched from quetiapine to perphenazine, a first-generation neuroleptic; her TD symptoms did not return.

After additional weeks free of TD symptoms she discontinued the acamprosate. Her TD symptoms returned, as did feelings of anxiety and agitation that had not been present while she was on the combination of acamprosate and perphenazine.

She resumed acamprosate, again finding that 666 mg three times a day did not give her complete relief, but 999 mg three times a day did. On this dose she again got relief of anxiety and agitation.

To test the hypothesis that the efficacy of acamprosate was related to adequate time above a threshold blood level the patient was asked to try taking 1332 mg of acamprosate once a day. On this dose she continued to be free of involuntary movements of TD, but did have significant GI side effects of diarrhea and abdominal cramps.

The results showed efficacy of acamprosate for TD at a lower total daily dose, when instead of distributing the dose evenly, a larger proportion of the dose was given at one time. This demonstrates that the use of acamprosate at a concentration above a therapeutic threshold value for a sufficient number of hours per 24-hour day (e.g., 6-14 hours, preferably about 8) is sufficient to give a 24-hour therapeutic effect.

Example 2

CASE 2: A 34-year old man had been treated with acamprosate for several years for TD due to exposure to several neuroleptics for schizoaffective disorder. He was currently treated with lamotrigine and quetiapine for his mental illness, and was taking acamprosate 1032 mg+999 mg+1032 mg on a three times daily basis. This dose of acamprosate completely relieved his involuntary movements of TD—the latter including involuntary movements of the cheeks and mouth, rocking movements of the trunk, and twisting movements of the both upper and lower extremities. 999 mg three times a day did not give full relief from his involuntary movements. To test the therapeutic threshold hypothesis the patient was asked to try 1032 mg of acamprosate once a day in the morning. On this dose he was free of movements in the morning and early afternoon but movements returned in the evening. When he added a second dose of 1032 mg in the late afternoon—8 to 10 hours after his first dose—he obtained complete relief of symptoms. He noted that when be got relief of his involuntary movements be also had less anxiety and agitation than when the movements were present.

Both of these cases support two hypotheses: 1) That the treatment response to acamprosate in TD (and presumably in other neuropsychiatric disorders characterized by recurrent unwanted stereotypic symptoms) is related to the amount of time the acamprosate level is above a specific threshold, and not on the AUC of the PK curve. This is so because in both cases the patient did better on regimens that had a lower total daily dose of acamprosate but higher individual doses. This is unexpected, because it has not been known heretofore that lower total daily doses of acamprosate could work better than higher ones if the former were given once or twice a day and the latter were given three times a day. (2) That the combination of acamprosate with a neuroleptic can provide relief of anxiety and agitation associated with psychosis and TD. This is unexpected, because though acamprosate by itself does not have anti-anxiety effects.

Combining the results from the dog study with the implications of the reported cases we can infer that acamprosate delivered by a GR system can relieve symptoms of TD and other neuropsychiatric disorders given once or twice a day. Considering the fact that the AUC from a single dose of acamprosate via a GR system can be more than twice the AUC from a single dose of the existing enteric-coated tablet formulation of acamprosate it appears that a total daily dose of less than one gram of GR acamprosate, given on either a once or twice a day basis would be adequate to treat TD in the case examples. Therefore in some cases—probably the majority of cases—of TD cases the minimum effective daily dose of acamprosate delivered by a GR controlled release system can be less than 1 gram—the minimum of the range of efficacious dosages reported heretofore for the enteric-coated formulation. It should be noted further that experience to date with the enteric-coated tablets has never shown them to fully relieve the symptoms of TD at doses of 1 gram, whereas here in some embodiments daily doses of less than 1 gram can offer complete symptom relief and not just a detectable therapeutic effect.

Example 3

A pharmacokinetic study was conducted in four dogs. Dogs were given immediate-release (IR) acamprosate capsules orally. On one day they were given a single capsule containing 325 mg of acamprosate. On another day one week later the dogs were given 325 mg of acamprosate divided into smaller doses administered every 30 minutes, as shown in Table 1 below.

Figure 2:
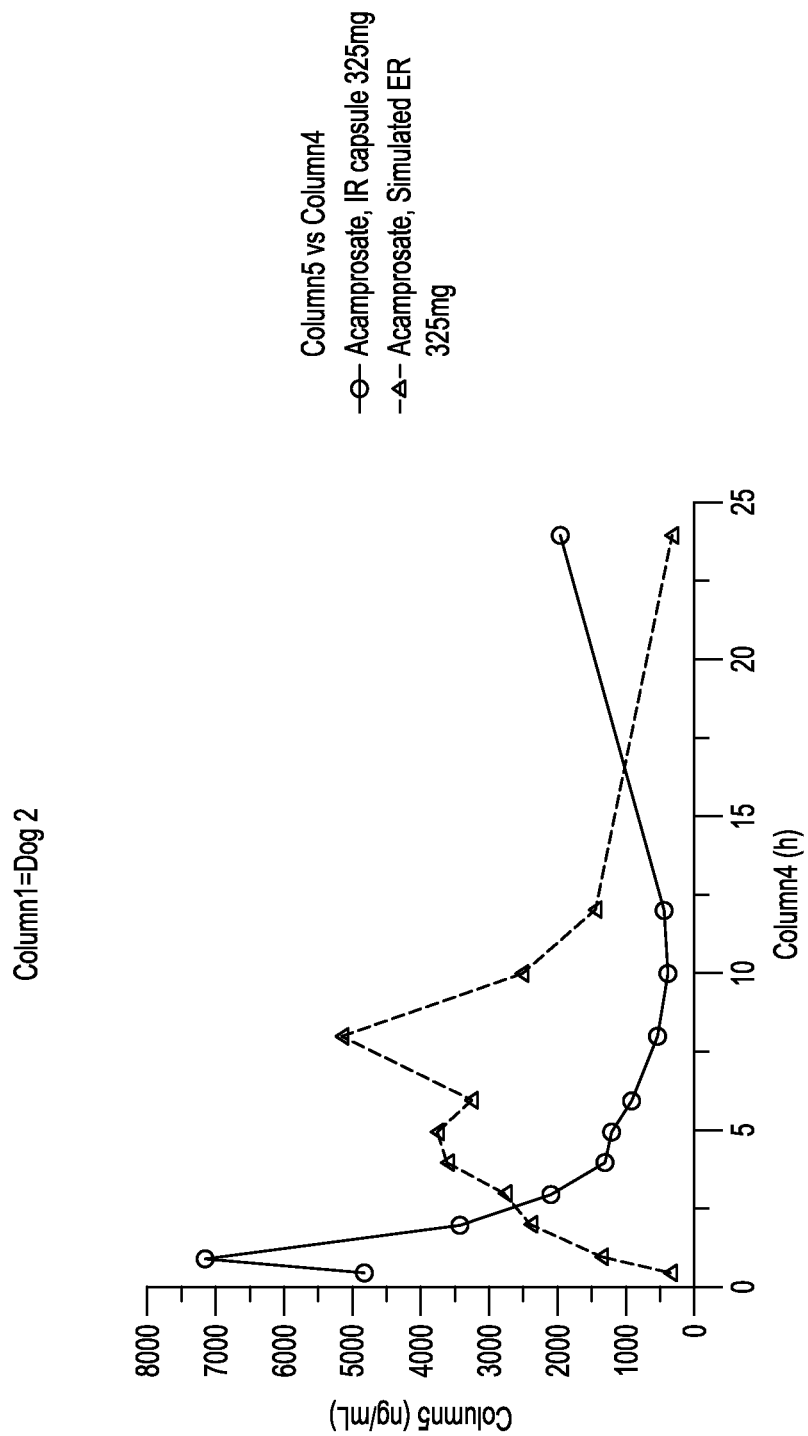
FIG. 2 illustrates the results for dog 2 from a pharmacokinetic study conducted in four dogs, which study is described below in EXAMPLE 3.
Figure 3:
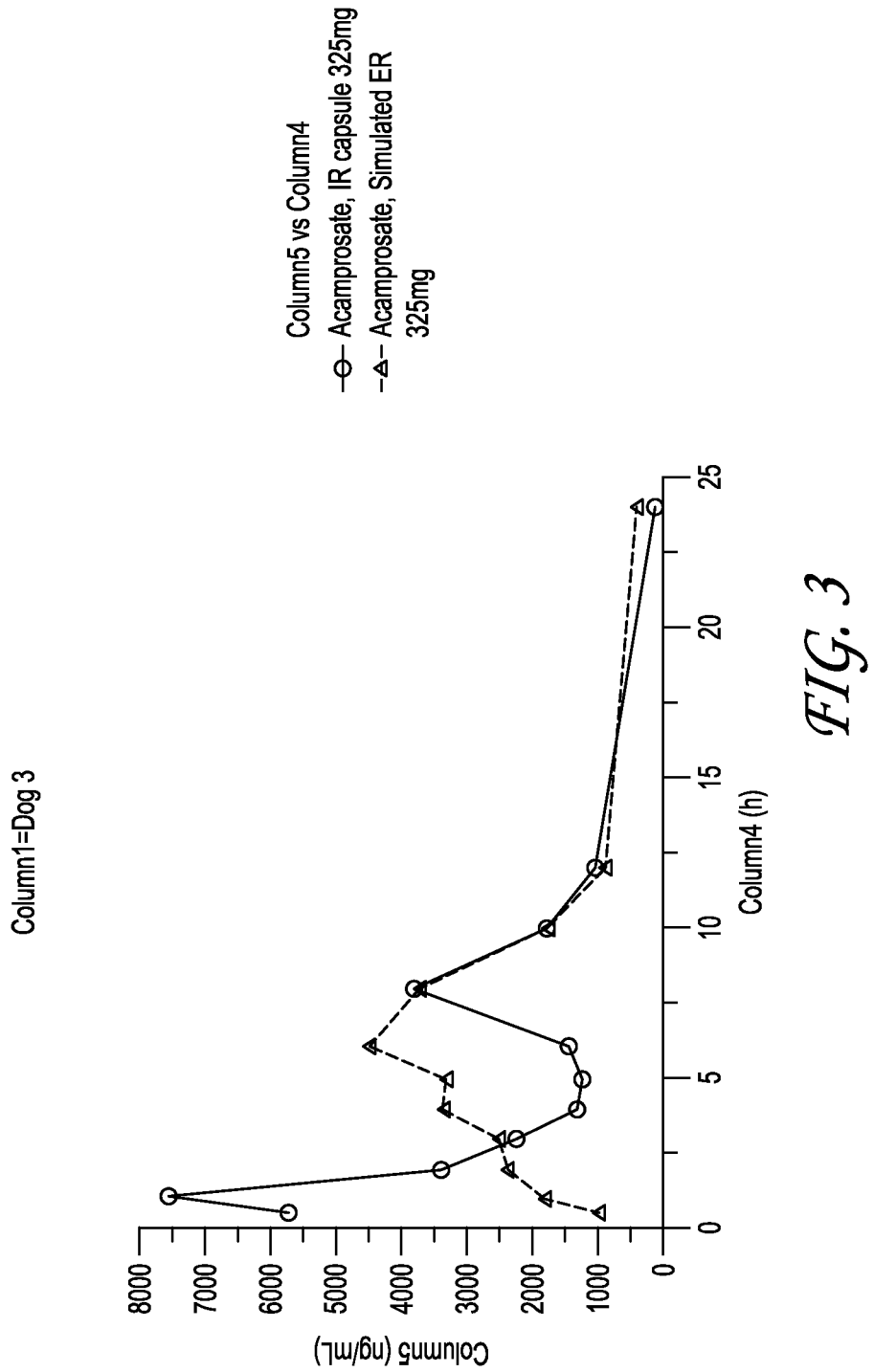
FIG. 3 illustrates the results for dog 3 from a pharmacokinetic study conducted in four dogs, which study is described below in EXAMPLE 3.
Figure 4:
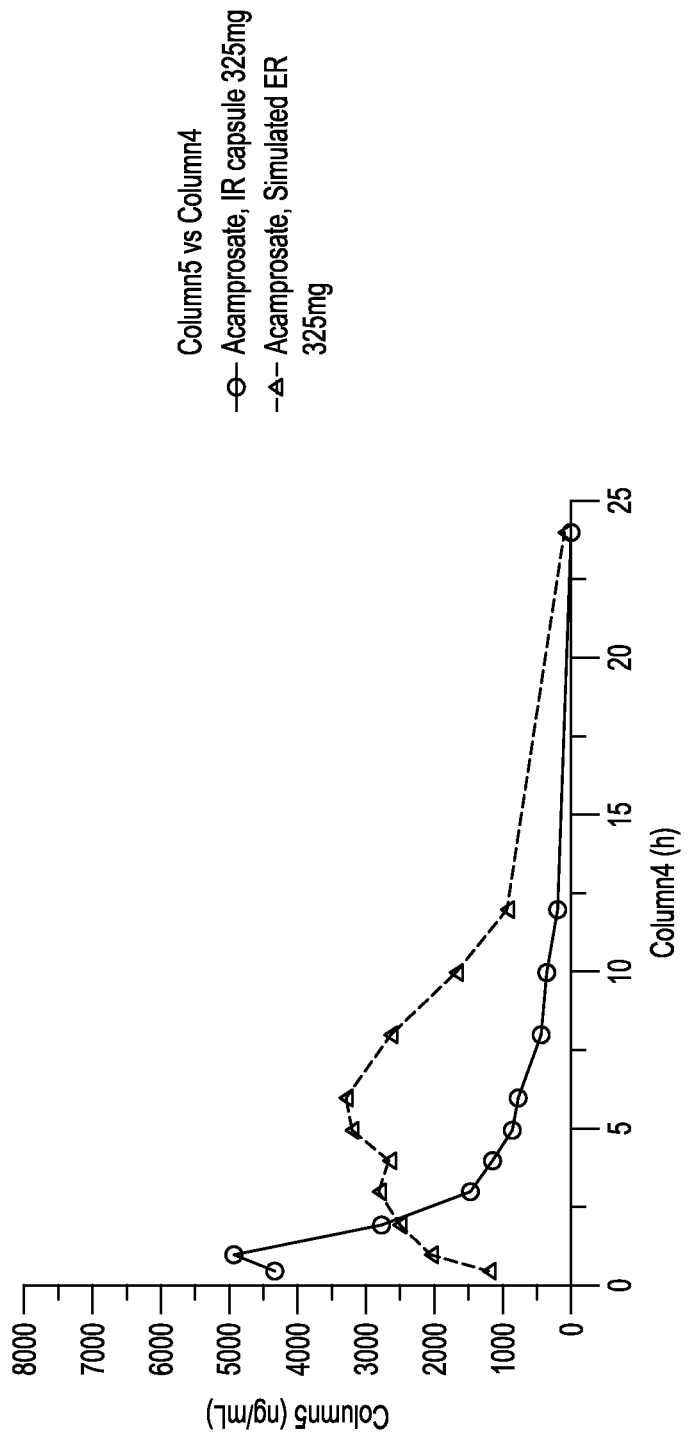
FIG. 4 illustrates the results for dog 4 from a pharmacokinetic study conducted in four dogs, which study is described below in EXAMPLE 3.

This mode of delivering acamprosate mimics the delivery of acamprosate into the stomach by a controlled-release GR system. FIGS. 1-4 are time-concentration curves for each of the dogs that compare IR acamprosate with simulated GR controlled-release acamprosate.

Table 2 shows pharmacokinetic parameters of the two delivery versions of acamprosate in each of the four dogs and displays ratios of interest between the two versions for several parameters of interest. In the table the residence time above two arbitrarily selected thresholds—2000 ng/mL and 3000 ng/mL was calculated by measuring the graphs; an asterisk next to the residence time indicates that the residence time comprised two discrete segments rather than a single contiguous period. The AUC was always greater for the simulated GR system, though the difference in two of the four dogs would be clinically insignificant. In one case the difference was more than twofold. These differences in a small sample are in accord with the well-known variability of acamprosate absorption between individuals. The $C_{max}$ was always significantly lower for the simulated GR system even when the AUC was significantly higher. The residence time above either of the two thresholds was significantly higher for the GR system.

TABLE 1

SIMULATION OF A GATRORETENTIVE CONTROLLED RELEASE SYSTEM BY HALF-HOURLY ADMINISTRATION OF IMMEDIATE RELEASE ACAMPROSATE

| Time (h) | Acamprosate Dosage (mg) |
| --- | --- |
| 0.0 | 81.2 |
| 0.5 | 33.6 |
| 1.0 | 25.8 |
| 1.5 | 21.8 |
| 2.0 | 19.2 |
| 2.5 | 17.3 |
| 3.0 | 15.9 |
| 3.5 | 14.8 |
| 4.0 | 13.9 |
| 4.5 | 13.2 |
| 5.0 | 12.5 |
| 5.5 | 12.0 |

TABLE 1-continued

SIMULATION OF A GATRORETENTIVE CONTROLLED
RELEASE SYSTEM BY HALF-HOURLY ADMINISTRATION
OF IMMEDIATE RELEASE ACAMPROSATE

| Time (h) | Acamprosate Dosage (mg) |
|---|---|
| 6.0 | 11.5 |
| 6.5 | 11.1 |
| 7.0 | 10.7 |
| 7.5 | 10.3 |
| Total dose | 324.8 |

TABLE 2

SELECTED PK PARAMETERS FROM DOG STUDY OF
IR VERSUS GR CONTROLLED-RELEASE ACAMPROSATE

| Treatment | Dog No | Tmax (h) | Cmax (ng/mL) | AUClast (h * ng/mL) | AUCinf (h * ng/mL) | Cmax/AUC | Hours over 3000 ng/mL | Hours over 2000 ng/mL |
|---|---|---|---|---|---|---|---|---|
| IR | 1 | 1 | 7380 | 31939 | 34283 | 23% | 2.6 | 3.5 |
| IR | 2 | 1 | 7150 | 31829 | 41542 | 22% | 2.4 | 2.9 |
| IR | 3 | 1 | 7550 | 35345 | 35739 | 21% | 1.8 | 2.6 |
| IR | 4 | 1 | 4920 | 15929 | 16029 | 31% | 1.8 | 2.6 |
| GR-CR | 1 | 5 | 4620 | 35185 | 35320 | 13% | 5.3 | 7.9 |
| GR-CR | 2 | 8 | 5140 | 44221 | 46714 | 12% | 6.8 | 9.7 |
| GR-CR | 3 | 6 | 4510 | 39182 | 43682 | 12% | 4.4 | 6.8 |
| GR-CR | 4 | 6 | 3290 | 32243 | 32806 | 10% | 2.6 | 8.8 |
| GR/IR | 1 | | 63% | 110% | 103% | | 200% | 225% |
| GR/IR | 2 | | 72% | 139% | 112% | | 288% | 330% |
| GR/IR | 3 | | 60% | 111% | 122% | | 250% | 256% |
| GR/IR | 4 | | 67% | 202% | 205% | | 150% | 333% |
| | | | Peak Ratios | Biovailability Ratios | | | Residence Time Ratios | |

Example 4

Table 3 lists gastroretentive (GR) technologies capable of delivering acamprosate so as to give a nearly constant level of the drug for four hours or more. Table 4 lists examples of controlled-release technologies that can be applied in conjunction with the gastroretentive technologies to produce the formulations utilized in embodiments described herein.

TABLE 3

GASTRORETENTIVE TECHNOLOGIES.

1) Floating - non-effervescent
2) Floating - effervescent
3) Bioadhesive
4) Mucoadhesive
5) Swelling
6) Expanding
7) Magnetic

TABLE 4

CONTROLLED-RELEASE TECHNOLOGIES.

1) Matrix
2) Coated beads
3) Osmotic
4) Ion exchange

Example 5

Composition of gastric retentive formulation of acamprosate calcium. The tablets swell when they come in contact with gastric juices; they are retained in the stomach for several hours if they are administered in the fed state (e.g., at the conclusion of a meal). The formulation has been manufactured as 400 mg and 800 mg tablets. These are standard round bi-convex white tablets with beveled edges. Both tablet strengths are spray coated with Opadry® II White (Colorcon, Inc.) for ease of swallowing. Purified water is the vehicle for the Opadry®; it evaporates during the coating process. The total weight of the coating is between 2% and 4% of the pre-coating weight.

The tablets prior to coating comprise the ingredients in the following table:

TABLE 5

| Ingredient | Function | Amount (mg) in 400 mg tablet | Amount (mg) in 800 mg tablet |
|---|---|---|---|
| Acamprosate calcium | Active ingredient | 400 | 800 |
| Povidone K-90 | Binder | 50 | 50 |
| Microcrystalline cellulose | Diluent | 320 | 100 |
| Colloidal silicon dioxide | Glidant | 10 | 10 |
| Citric acid | Acidulant | 60 | 0 |
| CARBOPOL ® 974P | Polymer | 60 | 60 |
| Carboxymethylcellulose | Polymer | 40 | 40 |
| STARCAP 1500 ® | Disintegrant | 40 | 40 |
| Talc powder | Filler | 10 | 10 |
| Magnesium stearate | Lubricant | 10 | 10 |
| Total prior to coating | | 1000 | 1120 |

Example 6

Dissolution profiles of the 400 mg and 800 mg GR acamprosate tablets. 400 mg or 800 mg tablets were dissolved in either acetate solution (pH 4.5) or 1N HCl (pH 1.0). The percentage of the active ingredient released into the solution was determined at 1, 2, 4, 6, 8, and 10 hours. Each release profile was assessed in six different test vessels. The following tables display the results, demonstrating that release is approximately linear with the square root of time. The fourth column in each table displays the amounts of drug that would be released if the release were exactly proportional to the square root of time, with a specified coefficient that ranges from 0.27 to 0.3.

TABLE 6

Release of Acamprosate from 400 mg Tablets of SNC-102 (Gastric Retentive Acamprosate formulation) in Acetate Solution (pH 4.5) - (n = 6)

| Time (hours) | SQRT Time | Mean % of Total Drug Released | 27% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 24.09 | 27.00 | 1.40 | 23 | 27 |
| 2 | 1.4142 | 36.09 | 38.18 | 2.34 | 34 | 40 |
| 4 | 2.0000 | 54.39 | 54.00 | 4.02 | 49 | 60 |
| 6 | 2.4495 | 70.11 | 66.14 | 4.15 | 64 | 76 |
| 10 | 3.1623 | 87.67 | 85.38 | 4.21 | 83 | 95 |
| 12 | 3.4641 | 92.31 | 93.53 | 4.38 | 87 | 99 |

TABLE 7

Release of Acamprosate from 400 mg Tablets of SNC-102 (Gastric Retentive Acamprosate formulation) in 0.1N HCl (pH 1.0) - (n = 6)

| Time (hours) | SQRT Time | Mean % of Total Drug Released | 27% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 31.60 | 27.00 | 1.58 | 24 | 27 |
| 2 | 1.4142 | 44.83 | 38.18 | 3.20 | 36 | 41 |
| 4 | 2.0000 | 63.20 | 54.00 | 4.42 | 56 | 62 |
| 6 | 2.4495 | 75.27 | 66.14 | 5.42 | 69 | 74 |
| 10 | 3.1623 | 91.31 | 85.38 | 3.59 | 85 | 91 |
| 12 | 3.4641 | 95.99 | 93.53 | 2.96 | 90 | 96 |

TABLE 8

Release of Acamprosate from 800 mg Tablets of SNC-102 (Gastric Retentive Acamprosate formulation) in Acetate Solution (pH 4.5) - (n = 6)

| Time (hours) | SQRT Time | Mean % of Total Drug Released | 30% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 31.60 | 30.00 | 1.58 | 29 | 34 |
| 2 | 1.4142 | 44.83 | 42.43 | 3.20 | 42 | 51 |
| 4 | 2.0000 | 63.20 | 60.00 | 4.42 | 58 | 64 |
| 6 | 2.4495 | 75.27 | 73.48 | 5.42 | 70 | 84 |
| 10 | 3.1623 | 91.31 | 94.87 | 3.59 | 87 | 97 |
| 12 | 3.4641 | 95.99 | 100.00 | 2.96 | 91 | 100 |

TABLE 9

Release of Acamprosate from 800 mg Tablets of SNC-102 (Gastric Retentive Acamprosate formulation) in 0.1N HCl (pH 1.0) - (n = 6)

| Time (hours) | SQRT Time | Mean % of Total Drug Released | 29% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 28.11 | 29.00 | 1.21 | 26 | 29 |
| 2 | 1.4142 | 41.56 | 41.01 | 1.77 | 40 | 44 |
| 4 | 2.0000 | 61.48 | 58.00 | 2.38 | 57 | 63 |
| 6 | 2.4495 | 75.41 | 71.04 | 1.61 | 73 | 77 |
| 10 | 3.1623 | 92.24 | 91.71 | 0.55 | 92 | 93 |
| 12 | 3.4641 | 96.62 | 100.00 | 0.65 | 96 | 97 |

Example 7

Combination of Reformulated Acamprosate with First-Generation Neuroleptics

First-generation neuroleptic (antipsychotic drugs) have been used for over 50 years in the treatment of schizophrenia and other psychotic disorders, as well as in the treatment and prevention of nausea and vomiting. The first of these drugs to be introduced to the market was chlorpromazine; others include thioridazine, perphenazine, trifluoperazine, haloperidol, fluphenazine, loxapine, and molindone. Their common feature is that they are all dopamine antagonists at both D2 and D3 dopamine receptors; each has its own distinctive set of effects on receptors for other neurotransmitters. One of the major drawbacks of these drugs is their propensity to cause movement disorders. With acute administration that can cause movement disorders including parkinsonism (tremor, rigidity, bradykinesia and gait instability) as well as dystonia, dyskinesia, and akathisia. Given chronically they can cause chronic movement disorders that persist even if the drug is stopped and may even be permanent. These disorders include tardive dyskinesia (TD), tardive dystonia, and tardive akathisia. The incidence of TD and other tardive movement disorders with long-term use of first-generation neuroleptics exceeds 25%, with an even higher rate in elderly patients. In part because of the very high risk of TD, a second generation of neuroleptics was developed that has a lower risk of causing TD and related movement disorders with chronic administration. These drugs include risperidone, quetiapine, clozapine, olanzapine, and aripiprazole. The incidence of TD with these drugs is less than 5%, but all are associated with metabolic side effects of sufficient severity to affect life expectancy. These side effects include weight gain, glucose intolerance, and disturbances in lipid metabolism. With the exception of clozapine the second-generation neuroleptics are not more effective in treating schizophrenia and other psychotic disorders. Clozapine, while more effective as treatment for severe mental illness, has additional serious medical side effects including a significant incidence of agranulocytosis that requires frequent monitoring of patients' white blood counts as a requirement for using the drug. The first generation neuroleptics, especially the higher-potency ones, have a much lower incidence of metabolic side effects than the second-generation neuroleptics, and some first generation neuroleptics, e.g., molindone, do not have them at all.

If first generation neuroleptics could be given without a high risk of causing or exacerbating tardive dyskinesia they would be preferable to second-generation neuroleptics for treating most patients with psychotic disorders as they would lack the troublesome metabolic side effects of the latter. Some embodiments herein relate to utilizing fixed-dose combinations of first-generation neuroleptics with new formulations of acamprosate designed for delayed release via a GR delivery system. Such combinations would not have been practical heretofore because of the high doses of acamprosate needed to treat TD if the existing enteric-coated tablet formulation is used. Given the compliance issues common among psychiatric patients a regimen of more than two pills daily would risk diminished effectiveness. If significantly more than a gram of acamprosate were needed to treat TD the combination of an effective dose of acamprosate for TD with an effective dose of a first-generation neuroleptic would need to be divided among at least three pills, as a dose of enteric-coated acamprosate significantly larger than 500 mg in a single pill might require that pill to be unpleasantly large, even without the addition of a second drug. The actual dosage of enteric-coated acamprosate needed to treat TD might in fact be much higher—more than 3 grams in some cases. On the other hand, if the needed dose of different formulation of acamprosate needed were less than one gram, treatment effective for both psychosis and TD could be delivered by one or two combination pills. Such is the case with the instant formulations described herein that provide for sub gram dosages and formulations of acamprosate.

While it is not the case that drugs that prevent a disorder will treat that disorder, it can be expected that that an effective treatment will attenuate the severity of the disorder, if it does not prevent it completely. In the two case examples, patients with established TD and a mental disorder took acamprosate together with a neuroleptic and had complete relief of their TD symptoms. Those patients would also be free of TD symptoms if they took the same combination without having TD at baseline. The incidence of TD will be lower if a first generation neuroleptic is co-administered with a dose of acamprosate that would be efficacious to treat established TD in the majority of patients. If TD did develop in some patients the severity would necessarily be less than if acamprosate were not given.

Some embodiments therefore relate to among other things the following two technologies: (1) Compositions containing a dose of a first generation neuroleptic adequate to treat a psychotic disorder and a dose of acamprosate adequate to treat tardive dyskinesia, including compositions in which the doses of the neuroleptic and the acamprosate are combined in a single pill, and compositions in which the doses are divided into multiple units delivered concurrently, e.g., one tablet of each drug in a single blister pack; and (2) The use of such compositions to treat one or more of schizophrenia, bipolar disorder, schizoaffective disorder, depression with psychotic features, delusional disorder, other psychotic conditions, the symptoms of hallucinations and delusions. The compositions in some aspects further can treat or prevent the symptoms of nausea and vomiting that often accompany the use of such medications. In the described technologies the use may be in patients with or without established TD.

It is surprising and unexpected that in some embodiments doses of acamprosate lower than the heretofore-described dosing range for treating TD can be effectively used, even though such lower doses may not have the same PK profiles as the enteric-coated pills utilized in previously-described treatment of TD—and such lower doses can in some embodiments produce a 24-hour AUC lower than that produced by similarly efficacious doses of enteric-coated acamprosate. Further, we note the unexpected finding that patients with TD and mental disorders who received acamprosate together with a neuroleptic showed an unexpected improvement in anxiety and agitation, even though acamprosate alone does not affect these symptoms.

It should be evident that the specific technology for formulating the GR delivery system for acamprosate does not matter; any system that can maintain an nearly constant level of acamprosate in the blood for four hours or more can be used.

Table 8 lists first-generation neuroleptic drugs and range of daily dosages at which they are usually prescribed. Some embodiments herein relate to tablets or capsules that implement one of the GR technologies in Table 9 delivering a dosage of acamprosate between 50 and 500 mg, together with a dose of one of the drugs described in Table 8 at one of the dosages specified in that table or a dosage of one-half of the minimum dose in the table below, and up to the maximum dose or any value there between. As an example, a tablet might comprise 4 mg of perphenazine together with 250 mg of acamprosate formulated in a swellable tablet, with the perphenazine surrounding a core of acamprosate.

TABLE 10

FIRST GENERATION NEUROLEPTICS AND METOCLOPRAMIDE: DAILY DOSAGES AND DOSES FOR FIXED-DOSE COMBINATION PILLS.

| Drug | Daily Dose Range | Example Single Pill Dosages in Combination with Acamprosate |
|---|---|---|
| Thioridazine | 10-200 | 10, 25, 50, 100 |
| Chlorpromazine | 25-200 | 25, 50, 100 |
| Thiothixene | 2-50 | 2, 5, 10, 25 |
| Trifluoperazine | 5-50 | 5, 10, 25 |
| Fluphenazine | 2-50 | 2, 5, 10, 25 |
| Haloperidol | 0.5-50 | 0.5, 1, 2, 5, 10, 20 |
| Perphenazine | 2-32 | 2, 4, 8, 16 |
| Loxapine | 10-100 | 1, 10, 25, 50 |
| Molindone | 10-200 | 10, 25, 50, 100 |
| Metoclopramide | 5-60 | 5, 10, 15 |

Example 8

Combination of Acamprosate with Second-Generation Neuroleptics

The dose of GR acamprosate can be between 100 mg and 800 mg. The principle is that the minimum dose is approximately one-half of the smallest currently-marketed dose of the drug. Examples of the dosage ranges of some non-limiting examples of first-generation neuroleptics are given in Table 10. Examples of dosage ranges for some second-generation neuroleptics are shown in the following Table 11. For example, the dosage for the neuroleptic can range from one-half of the minimum dose in the table below, and up to the maximum dose, or any value there between:

TABLE 11

| Neuroleptic | Minimum Dose | Maximum Dose |
|---|---|---|
| aripiprazole | 1 mg | 30 mg |
| asenapine | 1 mg | 10 mg |
| iloperidone | 1 mg | 24 mg |
| lurasidone | 10 mg | 120 mg |
| olanzapine | 1 mg | 20 mg |
| paliperidone | 1 mg | 12 mg |
| quetiapine | 12.5 mg | 400 mg |
| risperidone | 0.25 mg | 4 mg |
| ziprasidone | 10 mg | 80 mg |

Example 9

Combination of Acamprosate with SSRI and SSRI Antidepressants

SSRIs and SNRIs are efficacious in OCD and PTSD, both conditions that also can respond to treatment with acamprosate. Also, SSRIs and SNRIs are used to treat depressive and anxiety disorders in which recurrent, unwanted, stereotyped thoughts, perceptions, and behavior may be part of the syndrome. Since acamprosate and the serotonin reuptake inhibitors have different mechanisms of action, their therapeutic effects on these disorders can be synergistic. The fact that GR acamprosate can be efficacious at a daily dose of less than one gram a day, on a once or twice daily schedule, makes fixed-dose combinations of GR acamprosate with an SSRI or SNRI feasible.

The dose of GR acamprosate can be between 100 mg and 800 mg. Some embodiments relate to combinations where the minimum dose is approximately one-half of the smallest currently-marketed dose of the drug, for example one-half of the minimum dose in the table below, and up to the maximum dose or any value there between.

TABLE 12

| SSRI or SNRI | Minimum Dose | Maximum Dose |
|---|---|---|
| Citalopram | 5 mg | 40 mg |
| Desvenlafaxine | 25 mg | 100 mg |
| Duloxetine | 5 mg | 60 mg |
| Escitalopram | 2.5 mg | 20 mg |
| Fluoxetine | 5 mg | 40 mg |
| Fluvoxamine | 12.5 mg | 100 mg |
| Milnacipran | 6.25 | 100 mg |
| Paroxetine | 5 mg | 40 mg |
| Sertraline | 12.5 mg | 200 mg |
| Venlafaxine | 12.5 mg | 150 mg |

Example 10

Therapeutic Threshold

As noted herein, some embodiments relate to the novel and unexpected discovery that daily dosages of less than 1 gram of acamprosate can be formulated to effectively treat various conditions and disorders. In particular, some embodiments relate to formulations and dosage schedules that maintain the acamprosate concentration or blood level above a threshold for a sufficient time during each 24-hour period. Such formulations and schedules can be efficacious even though the acamprosate concentration does not exceed the threshold for the entire 24 hour period or even though the concentration or levels of acamprosate are very inconsistent (not at steady levels) during a given period of time such as a 24 hour period.

According to some embodiments, there are at least a number of parameters that can be adjusted to optimize clinical effectiveness while still keeping the total daily dose of GR acamprosate under 1 gram and limiting treatment to one or two pills daily: once or twice a day dosage; controlled release time (from 4 to 8 hours or any value between); retention time in the stomach; and dose of acamprosate (from 100 mg to 1000 mg). Those parameters are not meant to be limiting.

The following helps illustrate the concept. In a 2010 study, healthy volunteers were given 666 mg three times daily of enteric coated acamprosate tablets (Hammarberg et al.: Acamprosate Determinations in Plasma and Cerebrospinal Fluid After Multiple Dosing Measured by Liquid Chromatography—Mass Spectroscopy: A Pharmacokinetic Study in Healthy Volunteers. Ther Drug Monit 2010; 32:489-496). It took six days for steady state blood levels to be attained, after which the average level fluctuated between 760 ng/mL and 915 ng/mL. By contrast, after a single dose of 666 mg, the $C_{max}$ averaged 286 ng/mL. The authors note that the concentrations they observed were higher than those reported by other authors, citing for example a study of alcoholic patients who had a mean steady state concentration of 380 ng/mL on the 666 mg three times daily of the enteric coated formulation. It is likely given the efficacy of the 666 mg tid dose in the majority of patients, that the threshold steady state level for therapeutic efficacy in alcoholism is less than 500 ng/mL.

The threshold blood level for therapeutic efficacy in tardive dyskinesia (TD) and other neuropsychiatric disorders is generally believed to be no higher than 1000 ng/mL and generally not less than 300 ng/mL, as the doses used in the successful treatment of TD by the inventor have been between 2 and 4 grams daily.

In the dog study described herein, the subject animals typically weighing around 10 kg received a simulated GR dose of 324 mg with release proportional to the square root of time over 8 hours—100% of the drug delivered 7.5 hours after the start of the experiment. In this study the average time the concentration was above 2000 ng/mL after 8.3 hours. In view of the—(1) linearity of pharmacokinetics; (2) validity of extrapolating dosage on a mg/kg basis; (3) validity of simulated GR as a predictor of the function of an actual GR formulation; and (4) humans weighing 70 kg—the concentration of acamprosate above a therapeutic threshold of 500 ng/mL could be attained for 8 hours with a dose of GR acamprosate of (7*324)/4=567 mg.

While there can be inter-individual variability in body weight and the precise pharmacokinetic profile, a blood level above a therapeutic threshold for a human neuropsychiatric disorder can be maintained for eight hours after a single dose of GR acamprosate of less than one gram.

Thus, in some embodiments, a threshold value can an amount of a 300 ng/mL to 1000 ng/mL (or any amount of sub range there between) over a 4-8 hour period, preferable for about 5-7 hours, more preferably for a period of about 6 hours. For example, the threshold value that the acamprosate formulation can meet can be about 500-600 ng/mL for about 6 hours.

Some embodiments relate to acamprosate formulations and uses of the same where several hours of exposure—typically between 4 and 8 hours—to an adequate level of acamprosate can produce therapeutic effects on CNS function lasting for hours after the level of acamprosate falls—and often for the remainder of a 24 hour day. Thus, a single dose of GR acamprosate pill designed to release the drug over a 4-8 hour period can be sufficient to give a 24 hour therapeutic effect. Controlled release technology also can be utilized to ensure that a sufficient amount of acamprosate is released and available during a given time so as to keep the amount, concentration or level of acamprosate in the patient above the threshold.

Gastric retention in the fed state typically lasts about 4 hours. Thus, at the lower end of the controlled release interval of some embodiments of the technology (4 hours), the controlled release can take place almost entirely within the stomach. At the upper end of the interval the release can take place partly in the duodenum and possibly the upper jejunum. This may entail a partial loss of bioavailability, but only for the quantity of drug not yet released after 4 or more hours, it will apply to less than 50% of the total dose.

Those skilled in the art having the benefit of this application will appreciate that for treating a specific neuropsychiatric condition, the clinical response of a population can be optimized by selecting twice a day rather than once a day dosage, or by reducing the release time from 8 hours to 6 hours or 4 hours, for example. When a shorter exposure to the therapeutic level of acamprosate suffices for persistent efficacy, individual doses can be smaller, or, alternatively, the same dose can suffice for treating a condition that might otherwise require a higher dose if the release were over 8 hours, for example.

To attain the benefits of the GR formulation of acamprosate described in some of the present embodiments, the specific formulation preferably can release 90% or more of the acamprosate within 8 hours. On the other hand, at least 50% of the acamprosate is released within 3-4 hours, the typical time the pill (or other dosage form) will remain in the stomach if it is administered in the fed state. The latter criterion ensures that the GR preparation will be more bioavailable than enteric-coated acamprosate, and that it will approach the increased bioavailability seen with immediate-release acamprosate delivered directly to the stomach.

One of skill in the art also can titrate dosing to achieve a maintenance above a therapeutic threshold for a given patient. For example, a physician can titrate the dosage upward until a concentration greater than 50% of $C_{max}$ for 4-8 hours, preferably about 6 hours.

The fact that therapeutic efficacy can be achieved using acamprosate formulations of less than 1 gram daily with once or twice daily administration is surprising and unexpected. That is particularly true where the pK curve caused by the formulation maintains a steady concentration for only part of (generally for only 4-8 hours) a 24 hour period.

Example 11

Induction of Fed Mode Using Alpha-Lipoic Acid

In this example, alpha-lipoic acid is incorporated into a tablet for the purpose of increasing gastric retention time.

In a dog model, 125 mg of alpha-lipoic acid is administered 15 minutes before administration of swellable tablets containing acamprosate and labeled with barium sulfate. The treatment is performed largely as described in U.S. Pat. No. 7,405,238, the content of which is incorporated herein by reference in its entirety. The retention in the stomach of an 800 mg swellable tablet of maximum dimension 19.05 mm in four beagle dogs (weight 6 kg to 10 kg) is compared with the retention of such a tablet in either the fasting state or after a 50 gram meal. The results of the test with alpha-lipoic acid are summarized in the following table:

TABLE 13

| Condition | Minimum gastric retention time (hours) | Average gastric retention time (hours) | Maximum gastric retention time (hours) |
|---|---|---|---|
| Fasting | 0.5 | 0.9 | 1.7 |
| After 125 mg alpha-lipoic acid | 1.5 | 2.8 | 5 |
| After 50 g meal | 3 | 4.1 | 4.5 |

The data from this small sample of dogs support the notion that alpha-lipoic acid can significantly influence gastric retention time of an acamprosate-containing tablet, at dosages of alpha-lipoic acid that are small enough to be practicably incorporated into a tablet for consumption by a human patient, or to be incorporated into a coating for such a tablet.

Example 12

Human Administration of Acamprosate and Alpha-Lipoic Acid

In this example, alpha-lipoic acid is utilized as an immediate-release coating of a gastric-retentive tablet containing acamprosate as its active pharmaceutical ingredient.

A patient suffering from TD receives an effective but inconvenient treatment regimen of 3330 mg acamprosate daily, in the form of 10 enteric-coated tablets divided into three doses taken without food. This regimen is replaced by one of two tablets taken each morning on awakening or alternatively at bedtime, in either case on an empty stomach, each comprising 350 mg acamprosate in a GR formulation coated with 150 mg of an immediate-release formulation of R alpha-lipoic acid (it should be understood that the use of "R" alpha lipoic is not to be limiting; racemic alpha lipoic acid can also be used or any other form of the alpha lipoic acid as well). Almost all of the R alpha-lipoic acid passes through the duodenum before most of the acamprosate reaches the duodenum. The patient experiences adequate relief of TD symptoms compared to his normal regimen of enteric coated acamprosate (i.e., without gastric retentive formulation), and greatly improved convenience and treatment regimen adherence.

Example 13

In Vitro Demonstration of Persistent Effect of Acamprosate Exposure on Neuronal Response to Glutamatergic Stimulation The study is designed to test whether pre-treatment with acamprosate can have long-term neuronal protective effects against glutamate neurotoxicity. The study uses an in vitro organotypic hippocampal slice model. The study assesses whether less than 24 hours per day of exposure to a sufficient level of acamprosate can offer 24-hour therapeutic actions in neuropsychiatric disorders. The study demonstrates the persistent effect of exposure to acamprosate in protecting cultured rat hippocampus neurons from challenge with a toxic level of a glutamate agonist drug. This supports, among other things, the therapeutic use of acamprosate in neuropsychiatric disorders because the latter are related to the effect of acamprosate to decrease glutamate effects at NMDA and metabotropic glutamate receptors. The rat study shows that acamprosate has a persistent effect on some of the post-synaptic effects of glutamate agonists even after acamprosate has been removed from the culture medium for up to eight hours.

Hippocampal slices derived from 8-day-old Sprague Dawley rats are plated and subsequently exposed to a relatively acute (8 hour) or more chronic (5 day) acamprosate treatment. The slices are then removed from the medium containing acamprosate and returned to control medium for either 1 or 8 hours. The slices will then be challenged with either NMDA (50 uM) or a selective mGLuR1 or mGluR5 agent for 1 hr. The slices are then placed in normal medium with propidium iodide for 24 hr and assessed for neurotoxicity/neuroprotection as described below.

Methodology:

Preparing an Organotypic Hippocampal Slice Culture (OHSC):

Eight-day old Sprague-Dawley rat pups are used in all organotypic hippocampal slice experiments (OHSC) experiments. Pups are sacrificed (3 males/3 females per litter) via rapid decapitation, brains are then aseptically removed and transferred to ice-cold dissecting media. Following removal of the meninges, hippocampi are removed, sliced coronally at 200 μm and plated in triplicate onto 0.4 μm Biopore membranes. Membranes are suspended in 1 ml culture media using six-well plates. Plates are then incubated at 37° C. in a 5% $CO_2$/21% $O_2$/74% $N_2$ medical grade gas composition for 5 days in vitro (DIV) to allow affixture to the Teflon® membrane. Typically, 14-18 slices can be derived from each pup.

Acamprosate Pretreatment:

On the fifth day in vitro the plates are treated with new culture medium, with half exposed to 200 μM calcium acamprosate and half to normal medium for either 8 hr or 5 days. At this time, the plates are placed into fresh control medium for either 1 hr or 8 hr.

Glutamatergic Challenge:

At this time, the plates are placed either in fresh medium, medium with NMDA (50 uM) or a metabotropic glutamate receptor agonist for 1 hour.

Neurotoxicity/Neuroprotection Assessment:

For the final medium change, the plates are moved into normal media containing propidium iodide (PI) added to each well for 24 hours. PI only penetrates cell membranes of damaged or potentially dying cells, binding to DNA to produce a bright, intensified red fluorescence at 630 nm. The slices are visualized with SPOT Advanced version 4.0.2 software for Windows at a 5× objective with a Leica DMIRB microscope that is fitted for fluorescent detection using blue-green light, and connected to a personal computer through a SPOT 7.2 color mosaic. The emission wavelength of PI is 620 nm in the visual range; PI has a peak excitation wavelength of 536 nm. PI is excited using a band-pass filter exciting wavelengths between 510 and 560 nm. Intensity of the PI fluorescence is analyzed by densitometry using Image J and the pictures are quantified by detecting optical intensity of the CA1 pyramidal cell layer, CA3 pyramidal cell layer, and dentate gyrus granule cell layer of the hippocampus following background subtraction. Fluorescence is recorded in arbitrary units, then converted to percent of control, facilitating comparison across multiple cultures and controlling for variation between litters. PI uptake has been shown to correlate well with other measures of cellular injury and cellular death.

Example 14

Acamprosate is tested using a rat model of tardive dyskinesia looking at abnormal chewing movements produced in rats by exposing them for several weeks to haloperidol, a potent first-generation neuroleptic. First, acamprosate is tested and shows a steadily-maintained blood level will reduce or eliminate the abnormal movements. Rats then are dosed with acamprosate in a way that matches the therapeutic blood level for no more than 12 hours out of 24, to confirm that this reduces the involuntary movements.

Example 15

Acamprosate is tested in transgenic mouse models with movement disorders [(Per2(Brdm1) deletion or ENT1(−/−) mice or other mouse models] and hyperglutamatergic states. First, acamprosate is tested and shows a steadily-maintained blood level will reduce or eliminate the abnormal movements. Mice then are dosed with acamprosate in a way that matches the therapeutic blood level for no more than 12 hours out of 24, to confirm that this reduces the involuntary movements.

Example 16

The pharmacokinetic properties of the specific gastric-retentive (GR) preparation of acamprosate described in EXAMPLE 5 is tested in human subjects in two studies. In the first, subjects receive, 30 minutes after a standard high-fat meal, a single dose of 400 mg of GR acamprosate, of 800 mg of GR acamprosate, or of 666 mg of enteric-coated acamprosate. Plasma concentrations of acamprosate are determined at 1, 2, 4, 6, 8, 12, 24, and 48 hours afterwards and pharmacokinetic parameters are calculated.

In at least some subjects (a) $C_{max}$ and AUC are proportional to dosage for the 400 and 800 mg GR dosages, and (b) with respect to the 666 enteric-coated dosage, the GR formulations have higher bioavailability and a shorter $T_{max}$.

In the second study subjects receive 400 mg of GR acamprosate in the fasting state, in the fed state, and in the fasting state preceded (e.g., at least 10-15 minutes earlier) by 600 mg of R alpha lipoic acid.

In at least some subjects the pharmacokinetic curve (and the parameters AUC, $C_{max}$ and $T_{max}$) are similar for 400 mg of GR acamprosate in the fed state and for 400 of GR acamprosate in the fasting state preceded by R alpha lipoic acid; 400 mg of GR acamprosate in the fasting state without alpha lipoic acid shows a significantly lower AUC and lower $C_{max}$ than either of the other two conditions.

The herein described subject matter sometimes illustrates different methods, compositions and/or components contained within, or combined with, different other methods, compositions and/or components. It is to be understood that the various described methods, compositions, components and combinations of the same are merely provided as non-limiting examples, and that in fact many others can be implemented which achieve the same purposes and/or functionality.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the embodiments of the technology.

The publications discussed herein are provided solely for their disclosure prior to the filing date of the present application. Nothing herein is to be construed as an admission that the present embodiments are not entitled to antedate such publication by virtue of prior invention. Further, the dates of publication provided may be different from the actual publication dates which may need to be independently confirmed. The subject matter disclosed in the publications, including any methods, compositions, excipients (including ranges and dosages of the same), etc., are incorporated herein by reference in their entireties.

Many modifications and variations of the embodiments described herein may be made without departing from the scope, as is apparent to those skilled in the art. Also, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A tablet comprising:
   800 mg of acamprosate calcium or other pharmaceutically acceptable salt of acamprosate, distributed within a polymer matrix that comprises or consists of 60 mg of carbomer homopolymer type B.

2. The tablet of claim 1, wherein the tablet is small enough to be easily swallowed.

3. The tablet of claim 2, wherein the tablet is spheroid shaped.

4. The tablet of claim 2, wherein the tablet further comprises a neuroleptic or metoclopramide.

5. The tablet of claim 4, wherein the neuroleptic is selected from the group consisting of aripiprazole, asenapine, chlorpromazine, fluphenazine, haloperidol, iloperidone, loxapine, lurasidone, molindone, olanzapine, paliperidone, perphenazine, quetiapine, risperidone, thioridazine, thiothixene, trifluoperazine, and ziprasidone.

6. The tablet of claim 4, wherein the tablet further comprises metoclopramide.

7. The tablet of claim 5, wherein the neuroleptic is molindone.

8. the tablet of claim 5, wherein the neuroleptic is quetiapine.

9. The tablet of claim 5, wherein the neuroleptic is aripiprazole.

* * * * *